(12) United States Patent  
Neubauer

(10) Patent No.: US 11,380,186 B1  
(45) Date of Patent: Jul. 5, 2022

(54) SYSTEMS AND METHODS TO REDUCE ALARM FATIGUE

(71) Applicant: Marc Neubauer, Silver Spring, MD (US)

(72) Inventor: Marc Neubauer, Silver Spring, MD (US)

(*) Notice: Subject to any disclaimer, the term of this patent is extended or adjusted under 35 U.S.C. 154(b) by 0 days.

(21) Appl. No.: 17/506,673

(22) Filed: Oct. 21, 2021

Related U.S. Application Data

(60) Provisional application No. 63/246,441, filed on Sep. 20, 2021, provisional application No. 63/236,788, filed on Aug. 25, 2021, provisional application No. 63/214,409, filed on Jun. 24, 2021.

(51) Int. Cl.
| | |
|---|---|
| *G08B 21/02* | (2006.01) |
| *G08B 21/18* | (2006.01) |
| *G08B 7/06* | (2006.01) |
| *A61B 5/00* | (2006.01) |
| *A61M 5/172* | (2006.01) |

(52) U.S. Cl.
CPC ............ *G08B 21/182* (2013.01); *A61B 5/746* (2013.01); *A61M 5/1723* (2013.01); *G08B 7/06* (2013.01); *A61M 2205/18* (2013.01)

(58) Field of Classification Search
CPC ........ G08B 21/182; G08B 7/06; A61B 5/746; A61M 5/1723; A61M 2205/18
See application file for complete search history.

(56) References Cited

U.S. PATENT DOCUMENTS

| | | | |
|---|---|---|---|
| 7,432,807 B2 | 10/2008 | Schmitt | |
| 7,551,078 B2 | 6/2009 | Carlson | |
| 7,920,061 B2 | 4/2011 | Klein | |
| 10,242,060 B2 | 3/2019 | Butler | |
| 10,300,194 B2 | 5/2019 | Day | |
| 10,463,788 B2 | 11/2019 | Day | |
| 10,617,815 B2 | 4/2020 | Day | |
| 10,898,641 B2 | 1/2021 | Day | |
| 2006/0287885 A1* | 12/2006 | Frick | A61B 5/411 705/2 |
| 2008/0094227 A1* | 4/2008 | Becker | G16H 40/67 340/573.1 |
| 2009/0054735 A1* | 2/2009 | Higgins | A61B 5/0006 600/300 |
| 2014/0218202 A1* | 8/2014 | Wilson | G16H 40/67 340/686.6 |
| 2018/0310892 A1* | 11/2018 | Perschbacher | A61B 5/686 |
| 2019/0240405 A1 | 8/2019 | Wehba | |
| 2020/0020218 A1* | 1/2020 | Tezuka | G08B 21/182 |
| 2020/0121186 A1* | 4/2020 | Collins, Jr. | G06F 8/65 |

(Continued)

OTHER PUBLICATIONS

ECRI. Evaluation background: ancillary alarm notification systems. Health Devices Dec. 22, 2016.

(Continued)

*Primary Examiner* — Hongmin Fan

(57) ABSTRACT

A method for managing an alarm issued by a medical device being used to treat a patient is disclosed. The method includes the steps of receiving an alarm from the medical device, retrieving a dynamic attribute associated with the patient, assigning a sub-priority to the alarm based in part on evaluation of the dynamic attribute, and providing an alert to a staff member that is associated with the sub-priority.

11 Claims, 17 Drawing Sheets

(56) References Cited

U.S. PATENT DOCUMENTS

2020/0335209 A1    10/2020  Holscher
2021/0252210 A1     8/2021  Day

OTHER PUBLICATIONS

ECRI. Evaluation: Extension Engage ancillary alarm notification system. Health Devices Dec. 22, 2016.
Speich, Reducing Alarm Fatigue in the Intensive Care Unit: A Quality Improvement Research Study, (2017). Doctoral Disserlation, Uni of Conn.
Au-Yeung, Reduction of false alarms in the intensive care unit using an optimized machine learning based approach, Digital Medicine (2019) 2:86, Nature Partner Jounals, Sep. 15, 2019 (downloaded).
Delft Design Labs, Silent ICU—Intensive Care Alarm System, Joint Master Project Feb.-Jun. 2017.
McFarlane, Faster clinical response to the onset of adverse events: A wearable metacognitive attention aid for nurse triage of clinical alalms. (2018) PLoS ONE 13(5): e0197157. Published: May 16, 2018.
Vocera, product description for Engage: workflow engine, downloaded Sep. 2021.
Vocera, Solution Brief, Engage, downloaded Sep. 2021.

\* cited by examiner

SYSTEMS AND METHODS TO REDUCE ALARM FATIGUE

CROSS-REFERENCE TO RELATED APPLICATIONS

This application claims priority to U.S. Provisional Applications 63/246,241 filed on Sep. 20, 2021, 63/236,788 filed on Aug. 25, 2021, and 63/214,409 filed on Jun. 24, 2021, each of which is hereby incorporated in their entirety herein by reference.

BACKGROUND

Field

This disclosure relates to systems and methods of managing alarms of medical devices, particularly in a hospital.

Description of the Related Art

Alarms are an ever-present background in a hospital environment. Medical devices, e.g. patient monitors, ventilators, infusion pumps, etc., issue alarms for conditions that range from a routine need for service to life-threatening conditions. With conventional alarm priorities limited to "high," "medium," and "low," the criticality of any given alarm may not actually require the skill level of the person to whom the alarm is directed. Clinicians often find they are responding to conditions that do not require their skill level and could have been handled by a junior clinician. This results in a higher-than-necessary number of alarms being sent to the primary designated clinician. The sheer number of alarms received by such clinicians, particularly when the condition is not as serious as it appeared upon receipt of the alarm, exacerbates alarm fatigue.

Alarm fatigue can occur not just from the sheer number of alarms but also the loudness of audible alarms, the number of high-priority alarms that do not require an urgent response, and the duplicative efforts of sending the same alarm to multiple people. Alarm fatigue is also exacerbated by the great number of audible signals coming from alarms from different medical devices located in a patient's room. Most of the time, clinicians are not in the room and the medical device alarms continue to generate audible signals until a clinician arrives to respond. The audible signals create unnecessary noise that raises the anxiety and frustration of both patients and family members and causes an environment that does not promote patient healing.

SUMMARY

There is a need for an Alarm Management System that directs alerts to the lowest-level staff member who can handle the underlying conditions and reduces the number of audible alarms. It is further desirable to provide variable escalation time delays that are suitable for the criticality of the underlying condition. It is also beneficial to provide more information to the recipient of an alert.

In certain embodiments, a method for managing an alarm issued by a medical device being used to treat a patient is disclosed. The method includes the steps of receiving a first alarm from the medical device, retrieving a dynamic attribute associated with the patient, assigning a first sub priority to the first alarm based in part on evaluation of the dynamic attribute, and providing a first alert to a first staff member that is associated with the first sub priority.

In certain embodiments, a system for managing an alarm issued by a medical device being used to treat a patient is disclosed. The system includes a processor coupled to at least one of the medical device, a monitoring system being used to monitor the patient, and a hospital system. The system also includes a memory coupled to the processor. The memory contains data and instructions that, when loaded into the processor and executed, cause the processor to receive a first alarm from the medical device and retrieve one or more of first information from the medical device, second information from the monitoring system, and third information from the hospital system. One or more of the first, second, and third information includes a dynamic attribute associated with the patient. The data and instructions further cause the processor to assign a first sub priority to the first alarm based in part on evaluation of the dynamic attribute and provide a first alert to a first staff member that is associated with the first sub priority.

In certain embodiments, a method of communicating with a staff member is disclosed. The method includes the steps of receiving an alarm issued by a medical device being used to treat a patient, retrieving a dynamic attribute associated with the patient, selecting a first sub priority based in part on the dynamic attribute, and providing a first alert to a first staff member. The first alert includes a first identifier associated with the patient, a second identifier associated with the medical device, the alarm, a dynamic attribute associated with the patient, a value of the dynamic attribute, and a first sub-priority assigned to the alarm based on the dynamic attribute.

In certain embodiments, a method of silencing an alarm in a room of a patient is disclosed. The method includes the steps of receiving an alarm from a medical device, causing the medical device to stop emitting an audible alert, retrieving a dynamic attribute associated with the patient, assigning a sub priority to the alarm based in part on evaluation of the dynamic attribute, providing an alert to a staff member that is associated with the first sub priority, and causing, if the first sub-priority exceeds a threshold, an audible alert to be sounded in the patient room.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
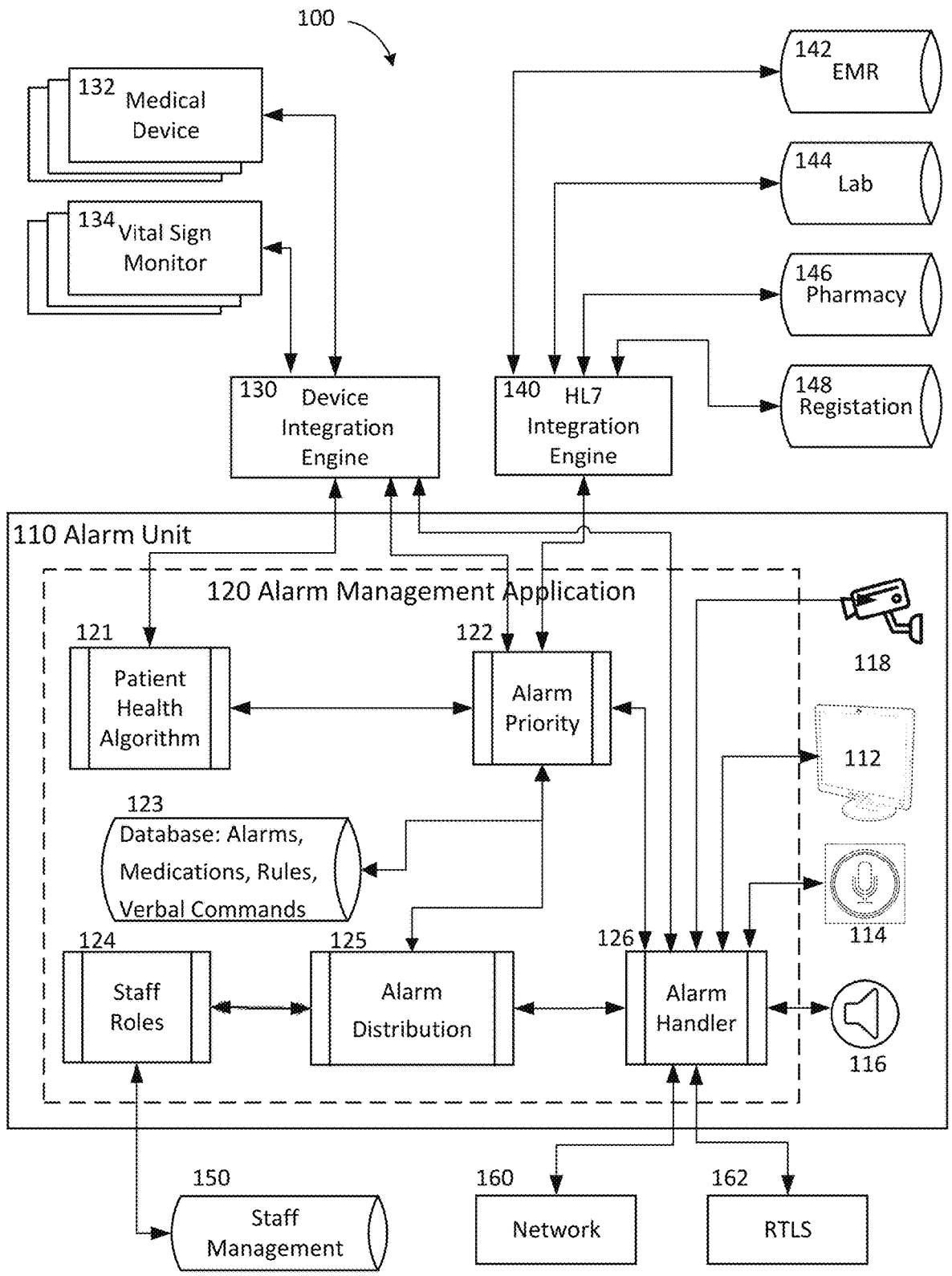
FIG. 1 is an exemplary block diagram of an Alarm Management System, according to certain aspects of the present disclosure.

The following description discloses a system and method that provides alarm sub-priority classes, a system and method of assigning sub-priorities based on the clinical need associated with the alarm, a system and method of selecting an alert recipient clinician or staff member having the skills necessary to resolve the alarm, and a system and method of dynamically adjusting the escalation and silencing of alarms.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. It will be apparent, however, to those skilled in the art that the subject technology may be practiced without these specific details. In some instances, well-known structures and components are shown in block diagram form to avoid obscuring the concepts of the subject technology. Like, or substantially similar, components are labeled with identical element numbers for ease of understanding.

As used within this disclosure, the term "alarm" refers to a signal received from a medical device indicating detection of a condition that requires attention by an operator or clinician. This term also may refer to a name or identifier associated with the detected condition.

As used within this disclosure, the term "alert" refers to a signal sent to a staff member and/or presented to the staff member, e.g. on a device in the patient's room or on a personal device) in an audible and/or visual manner.

As used within this disclosure, the phrase "personal device" refers to any means of receiving audible or visual communication, including but not limited to a pager, a phone, a watch, a two-way audio communicator, a tablet, a laptop, or a desktop computer. A personal device may be carried by the staff member, a mobile workstation, or located at a fixed location, e.g. a nursing workstation.

As used within this disclosure, the term "sub-priority" refers to a priority that is a further refinement of the conventional priorities of "high," "medium," and "low." The naming convention for sub-priorities used herein consists of a single letter associated with one of the conventional priorities. e.g. an "H," concatenated with a subdivision number, e.g. a "1," producing a sub-priority identifier, e.g. "H1." This term also includes other naming schemes, including replacement of the "H-M-L" set of names with larger number of discrete levels, including but not limited to numbers, e.g. 1-10, etc., letters, e.g. HHH, HH, H, etc., symbols, e.g. *, , *, etc., words, e.g. crisis high, crisis medium, crisis low, etc., or any combination therein, e.g. Crisis 1, Crisis 2, Crisis 3, etc.

As used within this disclosure, the phrase "treat the patient" or similar includes administering therapy from a device, e.g. infusion pump, ventilator, etc., and using a device to monitor or measure a patient health measurement, e.g. a patient monitor. This activity can be passive and only provide information.

As used within this disclosure, the phrase "dynamic attribute" refers to all changeable factors associated with a patient, that may influence association of a sub-priority with an alarm. Dynamic attributes can be broadly classified into factors associated with the patient, factors associated with a patient identifier, a diagnosis, or treatment of a patient, factors associated with medications or fluids administered to the patient, and factors associated with a device being used to treat a patient. Dynamic attributes include, but are not limited to, the examples listed in Table 1.

TABLE 1

| | | FACTOR | EXAMPLE |
|---|---|---|---|
| Patient Monitor Factors (currently being measured or periodically assessed) | | | |
| 1 | | patient health | |
| | a. | a patient health measurement | vital signs, labs, point of care parameter, diagnostic test result |
| | b. | change in the score of a patient health algorithm | Modified Early Warning Score (MEWS), Acute Physiology and Chronic Health Evaluation (APACHE) 2 |
| 2 | | an action by the patient | |
| | a. | detection of motion | patient motion detected directly at same time as alarm known to be induced by motion |
| | b. | loss of signal; abnormal signal | patient motion disconnects an EKG lead causing alarm for low pulse rate |
| Identification, Treatment, and Diagnostic Factors (from a hospital system) | | | |
| 3 | | a doctor's order | administer a medication (dose, method, frequency, etc.), specific settings of a medical device |
| 4 | | a patient instruction | a Do Not Resuscitate (DNR) order |
| 5 | | patient medical record | |
| | a. | a patient identifier | Age, gender, ethnicity, blood type, height, weight |
| | b. | a diagnosis of an underlying condition of the patient | heart disease, congenital heart defect, diabetes |

TABLE 1-continued

| | FACTOR | EXAMPLE |
|---|---|---|
| c. | an inherent characteristic of the patient | a genetic marker, an inherited condition, e.g. patient is a carrier of hemophilia |
| d. | whether patient has received a treatment that affects a condition | an implanted device |
| e. | whether a patient has previously experienced a symptom condition | note in electronic medical record for a (EMR) of fainting, dizziness, nausea |
| f | changes in a patient's condition | worsens or improves after an intervention |
| | Medication Factor (from medication library in a hospital system or standalone medication library) | |
| 6 | an indication for use of a medication or fluid being administered to the patient; | Vasopressors are indicated to raise blood pressure (BP) |
| 7 | characteristics of medication or fluid | |
| a. | intended effect | blood thinning medications indicated for patients with atrial fibrillation to reduce chance of stroke |
| b. | side effect | thyroid medication can cause very fast heart rate and irregular heart rhythm |
| c. | patient health measurement affected by a medication | vasopressors increase blood pressure, insulin lowers blood sugar |
| d. | pharmacokinetic or pharmacodynamic (PK/PD) characteristic | PK - e.g. biological half-life PD - e.g. drug-drug interactions |
| | Medical Device Factors (configuration or operational performance) | |
| 8 | a setting of the medical device | delivery rate of an IV fluid; oxygen content of delivered air |
| 9 | an operating mode of the medical device | running on battery power, ventilator set to allow spontaneous breathing |
| 10 | an operational status of the medical device | infusion pump has stopped infusing a fluid; a ventilator has stopped |
| 11 | a measured aspect of operation of the medical device | Measured battery voltage (indication of remaining operational time), tidal volume of each breath |
| 12 | whether there is a secondary mechanism to mitigate harm associated with alarm | tidal volume sensing as secondary indication of respiration if airway pressure alarm occurs, back-up battery |
| 13 | A feature of a device | Electrocardiogram (ECG) filter mode, number of leads used for monitoring |
| 14 | number of previous nonactionable or false alarms received before alarm received | high number indicates artifact, reliability issues, or environmental issues, e.g. electromagnetic interference |
| 15 | estimated time to perform a corrective action | replace a non-operational ventilator or pump |
| 16 | recommended replacement interval of a consumable | ECG leads should be changed 1x or 2x per day to reduce false alarms |

As used within this disclosure, the phrase "patient health measurement" refers to one or more of the following patient characteristics: a vital sign, a point-of-care (POC) observation or symptom, a diagnostic test, or a laboratory test. These measurements include but are not limited to body temperature, heart rate, blood pressure, respiration rate, tidal volume, blood oxygenation, blood glucose level, an arrhythmia, and end-tidal carbon dioxide ($ETCO_2$).

As used within this disclosure, the phrase "laboratory test" refers to analysis of a biological sample from the patient, e.g. blood. The analysis may be performed at the bedside or at a remote location.

As used within this disclosure, the phrase "patient health algorithm" comprises one or more of the following algorithms: a patient deterioration algorithm such as the MEWS, a patient pain algorithm, a patient disease severity algorithm, a patient awareness algorithm, a patient agitation algorithm, a patient deterioration algorithm, and a mortality score such as the APACHE 2.

A non-actionable alarm is one that does not require a clinical intervention or corrective action and includes false-positive alarms that indicate a given condition exists when it does not.

Staff Roles

Medical device alarms require clinicians or technicians to perform corrective action to address the cause of the alarm, improve patient outcomes, restore the device to normal functioning or replace the device with a functioning one. Corrective actions for clinical alarms are usually performed by clinicians, but technical alarms may be addressed by either clinicians or other staff, e.g. technicians, orderlies, etc.

In certain embodiments, the disclosed system defines multiple staff roles associated with levels of training and/or specific skills. Table 2 is an exemplary embodiment of defined staff roles. In this example, there are four clinical roles S1, S2, S3, S4 and a technician role S5. Primary care nurses, e.g. S2, perform most of the care of the patient, program medical devices, and address most alarms. In some settings, e.g. a surgical suite, specialists such as anesthesiologists, e.g. S1, program infusion pumps to administer anesthetics and controlled substances and will also address alarms. For ventilators, S1 may include respiratory therapists to troubleshoot complex situations and change ventilator and alarm settings. If the primary clinician, e.g. S2, is busy, then the Alarm Management System will forward the alarm information and sub-priority to a back-up clinician, e.g. S3, to ensure patient care needs are addressed in a timely fashion. S4 is defined as clinicians with less skill, e.g. LPNs, or less experience, e.g. medical students, new nurses in training, etc., who are capable of handling certain alarm conditions and can therefore relieve alarm fatigue of the S1-S3 roles. S5 is defined as technicians, staff, and orderlies who do not have a clinical background but are capable of resolving routine technical alarms.

TABLE 2

| Role | Training or skill |
|---|---|
| S1 | primary care physician, surgeon, anesthesiologist, respiratory therapist |
| S2 | primary care nurse |
| S3 | backup nurse |
| S4 | licensed practical nurse (LPN), medical student, new nurse in training |
| S5 | technician, staff, orderly |

In certain circumstances, for example a small hospital or clinic, there may be a limited number of staff and a single staff role, e.g. S2, may receive alerts for all sub-priorities. In larger facilities with a greater number and range of staff, the system of the present disclosure implements a risk-based approach to responding to alarms and associates different roles with different sub priorities. In certain embodiments, the primary clinician, e.g. the S2 role, is assigned a limited number of patients, e.g. 5 patients, and a secondary clinician, e.g. a S3 or S4 role, is assigned to provide back-up for a larger number of patients, e.g. 20 patients. With a larger patient to clinician ratio, the S4 clinician may be given lower sub-priority alerts with longer recommended response times as defined in Table 3 below.

Sub-Priorities

In certain embodiments, the disclosed system defines multiple sub-priorities. Table 3 provides an exemplary embodiment of defined sub-priorities. Although Table 3 describes nine sub-priorities, the disclosed system includes embodiments that provide more or fewer discrete sub-priorities.

TABLE 3

| Role | Recommended Response Time to Address Alarm | Condition |
|---|---|---|
| H1 | Immediate Response Required | immediate life-threatening condition |
| H2 | Within 1 minute | near-term life-threatening condition |
| H3 | Within 3 minutes | short-term risk of severe injury |
| M1 | Withing 5 minutes | need for immediate attention |
| M2 | Within 10 minutes | need for near-term attention |
| M3 | Within 15 minutes | device requires adjustment |
| L1 | Within 30 min | fault in primary system with a back-up system in operation |
| L2 | >> 30 min | requires near-term service |
| L3 | non-actionable | routine service |

In certain embodiments of the disclosed system, the system provides specificity for high priority alarms, enabling the notified clinician to determine whether they must drop what they are doing and immediately respond to an alarm to prevent patient harm, e.g. H1, or if the clinician has a few minutes to do so, e.g. H2 and H3. The alarm specificity provided in this disclosed system ensures that the highest sub-priorities are reserved for situations where the onset of life-threatening harm is immediate.

In certain embodiments of the present disclosure, one dynamic attribute is enough to define the sub-priority of an alarm. In other embodiments, one or more dynamic attributes are needed to define a sub-priority for a given alarm.

In certain embodiments of the present disclosure, an H1 sub-priority is assigned for an alarm associated with an infusion pump where all four of the following dynamic attributes are met: 1) the alarm stops the infusion, 2) the medication that is infusing is associated with a critical indication for use, 3) the medication affects a patient health measurement that is outside its normal range, and 4) the estimated time to perform a corrective action is greater than several minutes. A system error, e.g. a pump failure, alarm on an infusion pump that is infusing norepinephrine meets these four criteria since the system error stops the infusion, norepinephrine has a critical indication for use and it raises blood pressure for a patient with low pressure, and resolution requires a lengthy corrective active that involves retrieving a new pump, connecting to a patient, and reprogramming the infusion into the pump.

In certain embodiments, an H2 sub-priority is assigned for an air-in-line alarm on a pump infusing norepinephrine to a patient with low blood pressure. An air-in-line alarm stops the pump and norepinephrine has a critical indication for use and it affects a patient health measurement (it raises blood pressure for a patient with low pressure). An air-in-line alarm does not require a lengthy corrective action, however, and a nurse can resolve an air-in-line alarm by purging the line much quicker than getting a new pump, connecting the administration line, waiting for the replacement pump to start up, and reprogramming the pump. Addressing the air-in-line alarm in this way is routine and results in the patient being without a critical medication for less time, compared to the above example and warrants a lower sub-priority, e.g. H2.

In certain embodiments, an H3 alarm may occur when an air-in-line alarm is associated with morphine for treating pain. In this scenario only the first two criteria from the H1 example are met. The air-in-line alarm stops the infusion and morphine has a critical indication for use. However, morphine does not affect a patient health measurement or have a significant PK characteristic (i.e. short half-life). A patient not receiving morphine for a period of time is less critical than a patient not receiving norepinephrine and therefore a lower sub-priority, e.g. H3, is warranted for morphine.

In certain embodiments of the disclosed system, medium priority alarms can range between 3 to 15 minutes before the onset of potential harm is critical. In certain embodiments, M1 alarms have the potential to be high priority alarms that require action within a short time, e.g. 2 minutes, and it may be necessary for primary care nurses to always address these. In certain embodiments, M2 and M3 alarms have the potential to become M1 alarms within 5 and 10 minutes, respectively. This allows ample time for these alarms to be responded in an alarm forwarding scheme to reduce alarm fatigue while maintaining patient safety.

In certain embodiments of the disclosed system, low priority alarms take 15 minutes or greater before non-serious patient harm can occur. In certain embodiments, L1 alarms will escalate if clinicians do not respond to them. For example, a battery alarm with 30 minutes of life remaining that is initially assigned an L1 sub-priority will need to escalate if the device is not plugged into wall power within 15 minutes to allow time for escalation to a medium sub-priority and resolution by the escalation staff member. In another example, an L2 sub-priority escalates to a L1 sub-priority alarm after 30 minutes or does not escalate at all.

In certain embodiments, each sub-priority is categorized as a clinical alarm or a technical alarm and ranked based on one or more of time criticality and risk to the patient. The phrase "technical alarm" includes system error alarms or device fault alarms that often require a device to be replaced, e.g. a failure of the device's internal mechanism such as a stalled motor, and alarms that require a service to be performed on an operational device, e.g. replace a sensor, plug in battery, etc.

An example of a clinical alarm is an air-in-line alarm from an infusion pump because a clinically trained staff member needs to manipulate the intravenous (IV) set to purge the air bubble before restarting the infusion. Some alarm conditions require both technical and clinical corrective actions. For example, replacing a medical device will require the technical corrective action of bringing a new device into the patient's room and the clinical corrective action of connecting the device to the patient and programming the device.

Assignments of Staff Roles to Sub-Priorities

The present disclosure assigns a staff role to each sub-priority. In certain embodiments, certain staff roles, e.g. S5, have the skills to respond to technical alarms while other roles, e.g. S1-S4, have the skills and training to handle both clinical and technical alarms. A staff role assigned to a sub-priority is determined to be capable of resolving alarm conditions having this assigned sub-priority as well as alarm conditions assigned lower-level sub-priorities. In certain embodiments, the same staff role may be assigned to one of more sub-priorities. In certain embodiments, different staff roles may be assigned to the same sub-priority of alarm from different types of medical devices. Table 4 is an exemplary embodiment of different staff roles assigned to sub-priorities based on the medical device.

TABLE 4

| Medical device | Sub-priority | | | | | | | |
| --- | --- | --- | --- | --- | --- | --- | --- | --- |
| | H1 | H2 | H3 | M1 | M2 | M3 | L1 | L2 |
| infusion pump | S2 | S2 | S2 | S2 | S4 | S4 | S5 | S5 |
| Ventilator | S1 | S1 | S2 | S2 | S4 | S4 | S4 | S5 |
| device #3 | S1 | S1 | S2 | S2 | S2 | S4 | S4 | S5 |

In certain embodiments, an alarm has a unique escalation pathway. For example, a "low-battery" alarm is not initially a concern but will become a critical issue if the battery is allowed to become fully depleted. Table 5 is an exemplary escalation pathway for an infusion pump battery alarm. A battery alarm may be assigned a low sub-priority, e.g. L1, when there is 30 minutes of battery time left, escalated to a medium sub-priority, e.g. M2, when there are 15 minutes of life, and further escalated to a high sub-priority, e.g. H2, when there is 3 minutes left. The sub-priority conveys to the intended recipient how much time they have to respond to the alarm.

TABLE 5

| Remaining battery life (min, | Sub-priority |
| --- | --- |
| 30 | L1 |
| 15 | M2 |
| 3 | H2 |

The disclosed system reduces alarm fatigue since the primary care nurse, e.g. S2, is not responsible for responding to many sub-priorities of alerts unless escalated.

Escalation of Sub-Priorities

Escalation of an alert according to aspects of the present disclosure is adapted to the device issuing the alarm and the sub-priority of the alarm as defined by the dynamic attributes that affect it. An exemplary escalation pathway is shown in Table 6.

TABLE 6

| staff category | S4 | S4 | S2 | S2 | S3 | All |
| --- | --- | --- | --- | --- | --- | --- |
| Priority | M3 | M2 | M1 | H3 | H2 | H1 |
| escalation period | 5 min | 5 min | 2 min | 2 min | 1 min | Requires immediate response |
| next higher | S3 | S2 (a) | S2 (a) | S2 (b) | S1 | n/a |

S2 primary clinician assigned to this patient
S3 back-up clinician assigned to this patient
S4 lower-level clinician assigned to this patient The alarm escalation scheme in this invention can be applied to all medical device alarms to provide the specificity required to allow clinicians and technicians to know how much time they have to address the alarm before it escalates in sub-priority. In certain embodiments, an alert that has escalated in sub-priority is sent to a different staff member. In certain embodiments, the escalated alert is kept with the same staff member, but their personal device is updated to reflect the escalated status.

In certain embodiments, H1 sub-priority alarms never escalate in sub-priority. In certain embodiments, the next two sub-priority alarms, e.g. H2 and H3, escalate in one and two minutes respectively. In certain embodiments, M1 sub-priority alarms escalate in two minutes while the next two lower priority medium alarms, e.g. M2 and M3, both escalate in five minutes if not responded to. In certain embodiments, L1 escalates in 15 minutes. In certain embodiments, the highest escalation class for medium and low sub-priority alarms is H2. In certain embodiments, H1 alarms are reserved for situations that require a true immediate response.

System and Method

FIG. 1 is an exemplary block diagram of an Alarm Management System 100, according to certain aspects of the present disclosure. In certain embodiments, an alarm unit 110 is a physical device located in a patient room with its own display 112 and means to interact with a patient, e.g. speaker, microphone, video surveillance camera, etc. In certain embodiments, the Alarm Management System 100 is implemented as a virtual device, e.g. on a hospital server, and the alert content information is sent to a clinician's personal device, e.g. mobile phone. In certain embodiments, the alarm unit 110 is integrated by the control unit of a medical device, for example the controller of an infusion pump. The Alarm Management Application 120 contains data and instructions stored in a memory (not visible in FIG. 1) of the alarm unit 110 that, when loaded into a processor (not visible in FIG. 1) of the alarm unit 110 and executed, cause the processor to implement the functions described herein.

In certain embodiments, the Alarm Management Application 120 is communicatively coupled to a number of third-party, hospital-based systems. For example, the Alarm Management Application 120 will integrate with one or more of a Staff Management system 150, a Patient Registration system 148, an EMR system 142, a Lab system 144, and a Pharmacy system 146 that may include a Medical Administration Record (MAR). The Alarm Management Application 120 communicates information bidirectionally with these systems through a HL7 integration engine 140 ensuring that data from the hospital-based systems is translated appropriately for the Alarm Management Application 120 and vice versa.

The Alarm Management Application 120 communicates bidirectionally with a plurality of medical devices that alarm as exemplified by Medical Device 132, e.g. infusion pump, patient monitor, ventilator, etc. In the example of FIG. 1, this communication occurs through an integration engine 130 that translates the alarm information from these devices into a standard format for the Alarm Management Application 120. In certain embodiments, the Alarm Management Application 120 is connected to these other devices via a wired connection and a standard communication protocol, e.g. RS-232, RS-485, etc. In certain embodiments, a portion of the connection is wireless using one of the common medical device communication technologies, e.g. Wi-Fi. In certain embodiments, the Alarm Management Application 120 will also communicate with a Vital Sign Monitor 134. These physiological monitors provide information that is useful for determining the status of the patient and how the patient is responding to their treatment.

In certain embodiments, the Alarm Management Application 120 is also communicatively coupled to a communication network 160, which may include wired or wireless connections to various personal devices and other databases, and to a Real Time Locating System 162 (RTLS) that is capable of determining the physical location of a staff member; e.g. whether a staff member is in a patient room. In certain embodiments, the Alarm Management Application 120 is integrated into a third-party hospital enterprise system and the logic described in the present disclosure replaces the enterprise software's alarm management functionality.

In certain embodiments, the database 123 aggregates information related to the patient specific, device specific, and time dependent dynamic attributes. In certain embodiments, the database 123 includes information and rules regarding the alarms that are implemented in each connected Medical Device 132 and Vital Sign Monitor 134. This information includes the causes of the alarms, how the causes may be resolved, and the verbal commands the Alarm Management Application 120 can provide to a patient to resolve an alarm.

In certain embodiments, the database contains the medications and fluids being administered by a treatment device, e.g. an infusion pump, and medication administration information, e.g. the administered doses and times of administration, and the medical devices being used. This information may include PK properties, e.g. biological half-life, as well as whether an infusion is a loading dose, or a maintenance dose as determined by one or more of the doctor's orders and medical device settings. This information may also include PD characteristics, e.g. whether the medication or fluid is known or intended to affect a patient health measurement, e.g. vital sign or lab test of the patient.

In certain embodiments, the database 123 mirrors patient-related data available from one or more of the external systems, e.g. the EMR 142, the Lab 144, the Pharmacy 146, and the Registration 148. In certain embodiments, the Alarm Management Application 120 retrieves information on the patient such as their age and weight from the Registration system 148 so as to customize the sub-priority alarm criteria for that patient. For example, an alarm associated with an infusion pump stopping fluid replacement in a dehydrated adult may require less urgency than an alarm associated with an infusion pump stopping fluid replacement in dehydrated neonates or pediatrics under a certain weight. Where an H2 alarm may be appropriate for the adult with dehydration, an H1 alarm may be the preferred sub-priority alarm for the dehydrated neonate or pediatric under a certain weight.

In certain embodiments, information about the patient from the Device Integration Engine 130 is drawn into a Patient Health Algorithm module 121 that is configured to execute an assessment protocol that combines various measurements and/or assessments to generate a "health rating" that can then be transferred to the Alarm Priority function 122 for use in assigning a sub-priority. In certain embodiments, the protocol may be one or more of the MEWS, which is a tool designed to identify patients with declining conditions, and APACHE 2, a widely used intensive care unit (ICU) mortality prediction tool.

In certain embodiments, the Alarm Management Application 120 utilizes a nationally known patient health algorithm 121, or algorithms customized by the individual hospital, to dynamically adjust the sub-priority assigned to an alarm. Two such algorithms are the MEWS and the National Early Warning Score (NEWS) algorithms, which assign a scope to certain vital signs based on a comparison to respective thresholds, wherein higher scores area associated with poorer prognosis. These algorithms are used to triage patients in a lower acuity setting and determine the need for a rapid response team to intervene. In certain embodiments, the Alarm Management Application 120 calculates the algorithm score based on vital signs received from a Vital Sign Monitor 134 and dynamically adjusts the sub-priority of an alarm related to a medication or fluid that may improve the patient's deteriorating condition. For example, if a patient is experiencing decline in several parameters that may indicate the onset of sepsis and the patient is receiving fluid replacement therapy or an antibiotic, then the Alarm Management Application 120 may increase the sub-priority of an "infusion stopped" alarm by one or two levels.

When an alarm is received from a Medical Device 132, the Alarm Priority module 122 determines the sub-priority for the alarm condition based in part on one or more dynamic attributes, for example information received from the Vital Sign Monitor 134 and information retrieved from one or more of the EMR 142, the Lab system 144, the Pharmacy system 146, and the Registration system 148 as well as information, e.g. medication, from the database 123. The Alarm Priority module 122 determination may also be based in part on alarm information and rules retrieved from the database 123.

Once the sub-priority is assigned to the alarm, the Alarm Priority functionality 122 sends the information to the Alarm Distribution functionality 125. The Staff Role functionality 124 will retrieve the current shift's clinicians and staff/technicians from the hospital's Staff Management system 150, associate the available staff members with defined staff roles, and send this information to the Alarm Distribution functionality 125. The Alarm Distribution functionality 125 will combine the sub-priority with the appropriate staff role, identify the clinician or technician associated with the role and assigned to the patient, and send the sub-priority and role and staff member identification to the Alarm Handler 126.

In certain embodiments, the Alarm Handler 126 will determine from the RTLS 162 if there is an assigned clinician or technician is in the patient room. In certain embodiments, if a staff member is not in the room then the Alarm Handler module 126 provides an alert to the staff member associated with the staff role assigned to the sub-priority through the network to one or more of the staff member's personal devices.

In certain embodiments, the Alarm Management System 100 comprises a second application (not shown in FIG. 1) that is installed locally on the personal device. In certain embodiments, a set of specific escalation rules, e.g. rules governing how much time before one sub-priority escalates to another, rules associated with how dynamic attributes are applied across a user population, etc., for this patient are downloaded onto the personal device and the local app can execute escalation of a received alert per the downloaded rules. In certain embodiments, updates to the specific escalation rules are periodically downloaded to the personal device.

In certain embodiments, the Alarm Unit 110 includes a display 112, a microphone 114, an audio annunciator 116, e.g. a speaker or a buzzer—and a video surveillance camera 118. In certain embodiments, the Alarm Handler functionality 126 will provide one or more of a visual alert on the display 112 or an audio alert on the annunciator 116 according to information received from the Alarm Distribution module 125. In certain embodiments, a microphone or video surveillance camera is used to detect patient actions that assist the Alarm Management Application 120 to verify the presence or the lack of presence of a particular cause of an alarm to help determine the appropriate sub-priority or to determine the alarm can be suppressed, e.g. a false positive alarm that does not need to be conveyed to the intended recipient.

The Registration system 148 may disclose that the patient has a Do Not Resuscitate (DNR) order. In certain embodiments, sub-priority assignment rules in the Alarm Priority functionality 122 determine alarms for patients with a DNR order are assigned lower sub-priorities that the same alarms for patients without a DNR order. For example, an H1 sub-priority will be changed to H2, a H2 sub-priority to H3, etc. In certain embodiments, only the highest sub-priority, e.g. H1, will be reduced and all other assigned sub-priorities remain at the standard level.

In certain embodiments, the escalation rules are different when a clinician is in the patient room. In certain embodiments, the Alarm Distribution module 126 communicates to the Medical Device 132 and causes the Medical Device 132 to emit or silence the alarm. In certain embodiments, every alert for all alarms will cause an alert in the patient's room, either from the Alarm Unit 110 or the Medical Device 132, after a defined amount of time.

Alert Content

The method disclosed herein enhances the ability of a staff member to determine the urgency of responding to an alarm and the amount of delay time they may have before responding to an alarm.

In certain embodiments, the content provided to a personal device or for the display screen for an in-room Alarm Management System for an original alert includes one or more of the following: the original sub-priority, the time remaining until the sub-priority is escalated, the identification, e.g. initials, of the staff member to whom the alarm will be escalated, the highest sub priority that is associated with the escalation staff member, whether a back-up is available for the escalation staff member, and a corrective action or recommendation based on a dynamic attribute that may be useful to the recipient. For example, if a dynamic attribute indicates a critical arrhythmia exists and the patient is on a medication that is known to cause the arrhythmia, then the alert includes information that a medication with potential adverse effects to the present condition is being administered to the patient.

For an escalated alert, additional information includes the original sub-priority juxtaposed with escalated sub-priority, e.g. M1/H3, and the time since the alarm was received. Inclusion of the original sub-priority in an escalated alert informs the recipient of the severity of the original alarm and helps staff members determine how to triage concurrent alarms from different patients.

Figure 2A:
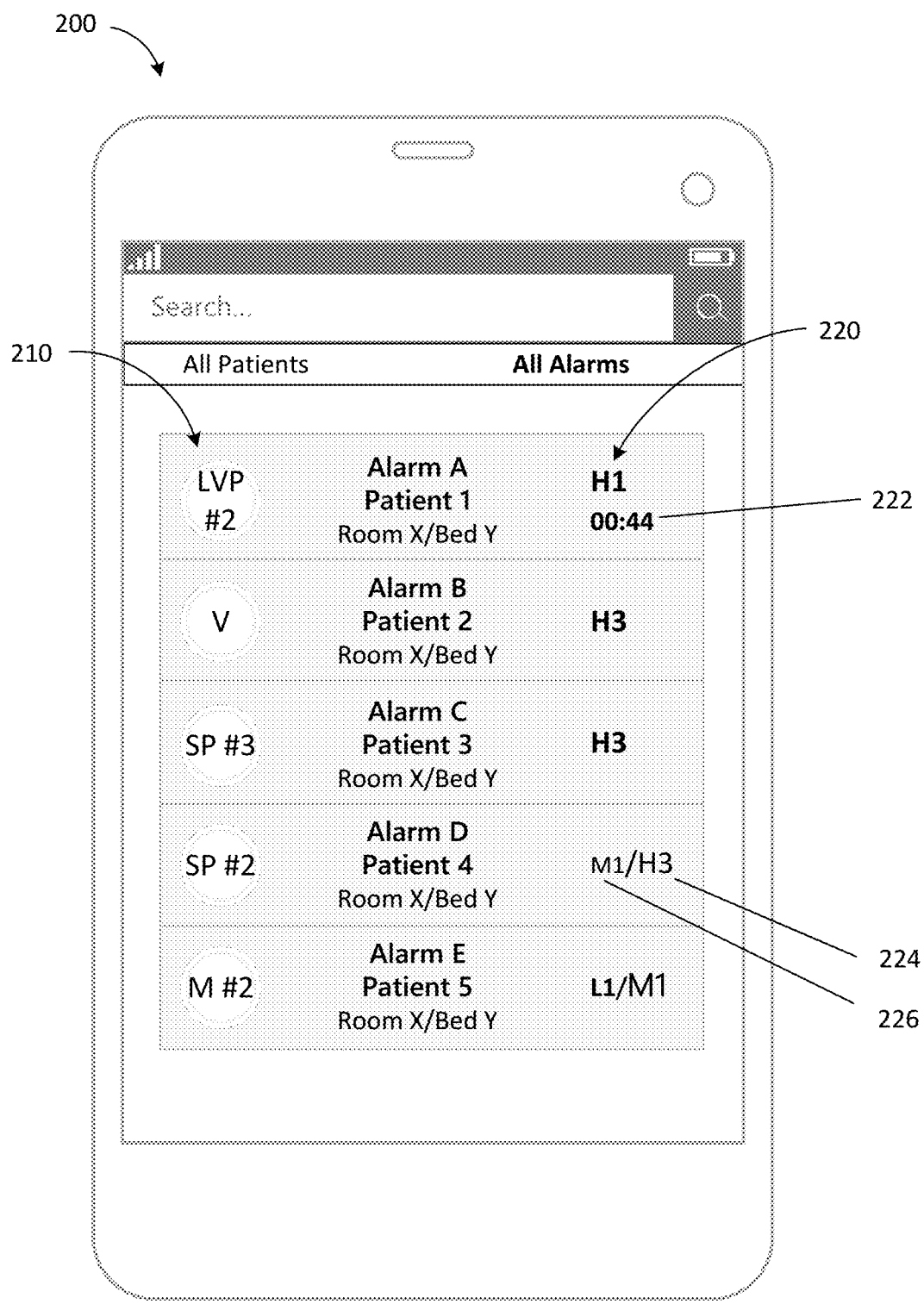
FIGS. 2A and 2B are exemplary embodiments of alerts provided on a staff member's personal device, according to certain aspects of the present disclosure.
Figure 2B:
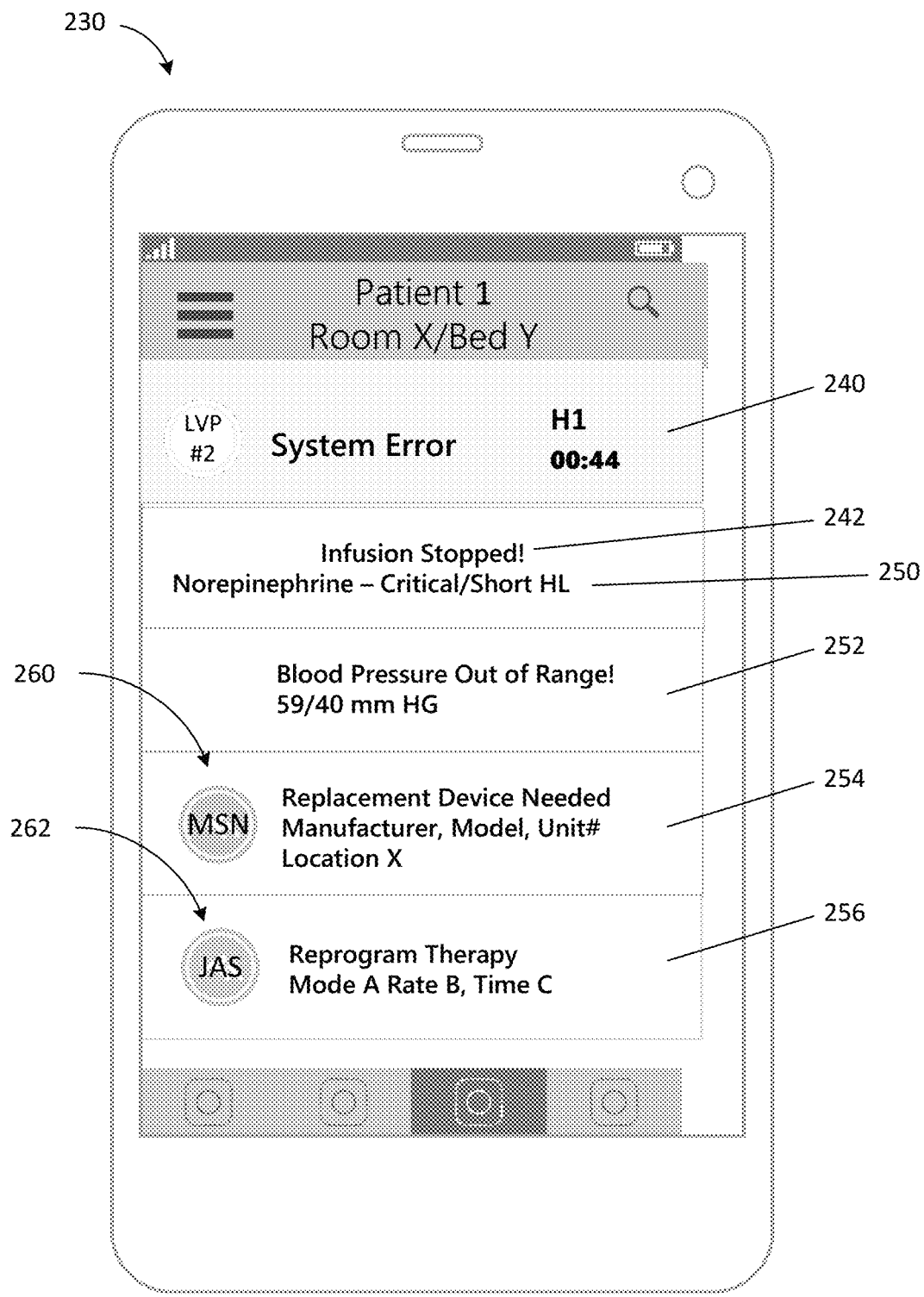

FIGS. 2A and 2B are an exemplary embodiment of a method of providing a first alert to a first staff member's personal device based in part on a dynamic attribute of a patient. In certain embodiments, the visual display of the information depicted in FIGS. 2A and 2B is information that can also be conveyed on a display 112 of the Alarm Management System 100 located in a patient's room.

FIG. 2A depicts an exemplary display 200 of a list of alarms on the personal device of a staff member. On the left-hand side is the device identification information 210, e.g. LVP—large volume pump, V—ventilator, SP—syringe pump, and M—monitor. In the middle of each alarm entry is the alarm display name, and patient identification information, e.g. name, room, bed, etc. On the right-hand side of each entry is the sub-priority or sub-priorities 220. The sub-priority information contains either the sub-priority or the original (i.e. before escalation) sub-priority 226 juxtaposed with the escalated current sub-priority 224. For example, the Alarm E started as a L1 sub-priority alarm and has escalated several times and is now a M1 sub-priority.

In certain embodiments, the alarms are listed in order of importance with the alarms associated with the highest sub-priority 20 listed first, e.g. H1. In certain embodiments, ventilator alarms will be displayed first. In other embodiments, patient monitor alarms associated with a critical arrhythmia will be displayed next especially if there is a current treatment, e.g. medication infusion, that may be causing the arrhythmia. In other embodiments, infusion pump alarms will be displayed after ventilators alarms and critical arrhythmia alarms but will otherwise be displayed before monitor alarms. In the example of FIG. 2A, Alarm B associated with a H3 ventilator alarm is displayed before Alarm C, a H3 syringe pump alarm. In certain embodiments, the original sub-priority of two alarms are compared and the alarm associated with the higher original sub-priority alarm is displayed first. In FIG. 2A, Alarms C and D are both currently H3 alarms, however Alarm C has the higher original sub-priority and is displayed first.

FIG. 2B provides an exemplary display 230 of expanded information for one of the alarms of FIG. 2A, the system error alarm 240 for a large volume pump with a H1 sub-priority. The alarm content shows both the dynamic attributes associated with the alarm and corrective actions associated with the dynamic attributes. For example, the display provides 1) dynamic attribute 242—a medical device factor that the infusion has stopped, 2) dynamic attribute 250—a medication factor that the medication has a critical indication-for-use, and 3) dynamic attribute 252—a patient monitor factor that a patient health measurement, e.g. blood pressure, affected by the medication is out of its range, e.g. 59/40 is a very low blood pressure. The display 230 includes two corrective actions: the first action 254 is retrieve a new pump with the pump ID and location information provided. The initials 260 identify the staff member assigned to execute this action. The second corrective action 256 is for the clinician 262, "JAS," to reprogram the pump and provides the reprogram instructions.

Table 7 illustrates an exemplary alert content.

TABLE 7

|  | Initial alarm | Escalated Alarm |
| --- | --- | --- |
| Alert Recipient | Primary Nurse - MJK | Primary Nurse - MJK |
| Current sub-priority | H3 | H3/H2 |
| Next sub-priority | H2 | H1 |
| time remaining to escalation | 2 min | 1 min |
| Expected Escalated Person | Back-up nurse - LSM | Back-up nurse - LSM |
| Escalated Person's highest sub-priority alarm | M1 | H1 |
| Back up available? | Yes | No |

Table 7 juxtaposes information from an initial alarm and an escalated alarm and shows how a change in time affects how the alert conveys information and how the availability of a backup may change. The initial alarm is sent the primary nurse with the initials MIK as a H3 sub-priority alert. In certain embodiments, the time to escalate between a H3 to H2 alarm takes 2 minutes. In certain embodiments the primary nurse has the option to send this alarm to the back-up nurse, having the initials of "LSM," since the highest sub-priority of the back-up nurse is M1.

For the alert that shows the escalated alarm, the sub-priority would show as H3/H2 where the H3 was the original sub-priority and the H2 is the current and escalated sub-priority. The time before escalation from an H2 to an H1 sub-priority alarm is one minute. During the time it took for the H3 alarm to escalate to an H2 alarm, e.g. two minutes, the back-up nurse with the initials LSM received an H1 sub-priority and is not available as a back-up since they have a more urgent alarm to respond to. In certain embodiments, the back-up staff member will not be available. In other embodiments, if the back-up nurse "LSM" was not available then the Alarm Management Application 120 would show the availability of another back-up staff member who is available.

Infusion Pump Alarms

Figure 3A:
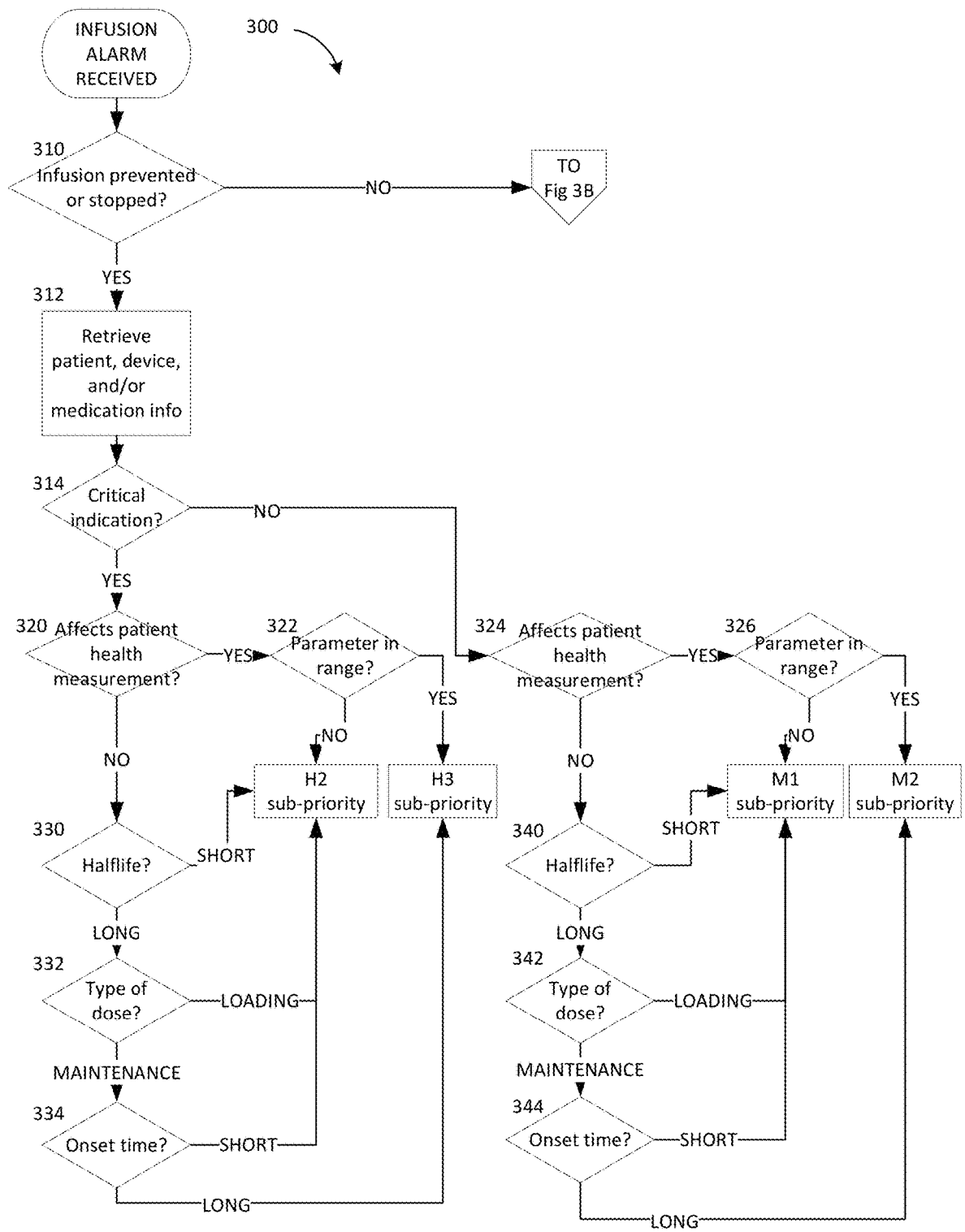
FIGS. 3A and 3B depict a flowchart of an exemplary embodiment of a method of assigning a priority and sub-priority to an alarm received from an infusion pump, according to certain aspects of the present disclosure.
Figure 3B:
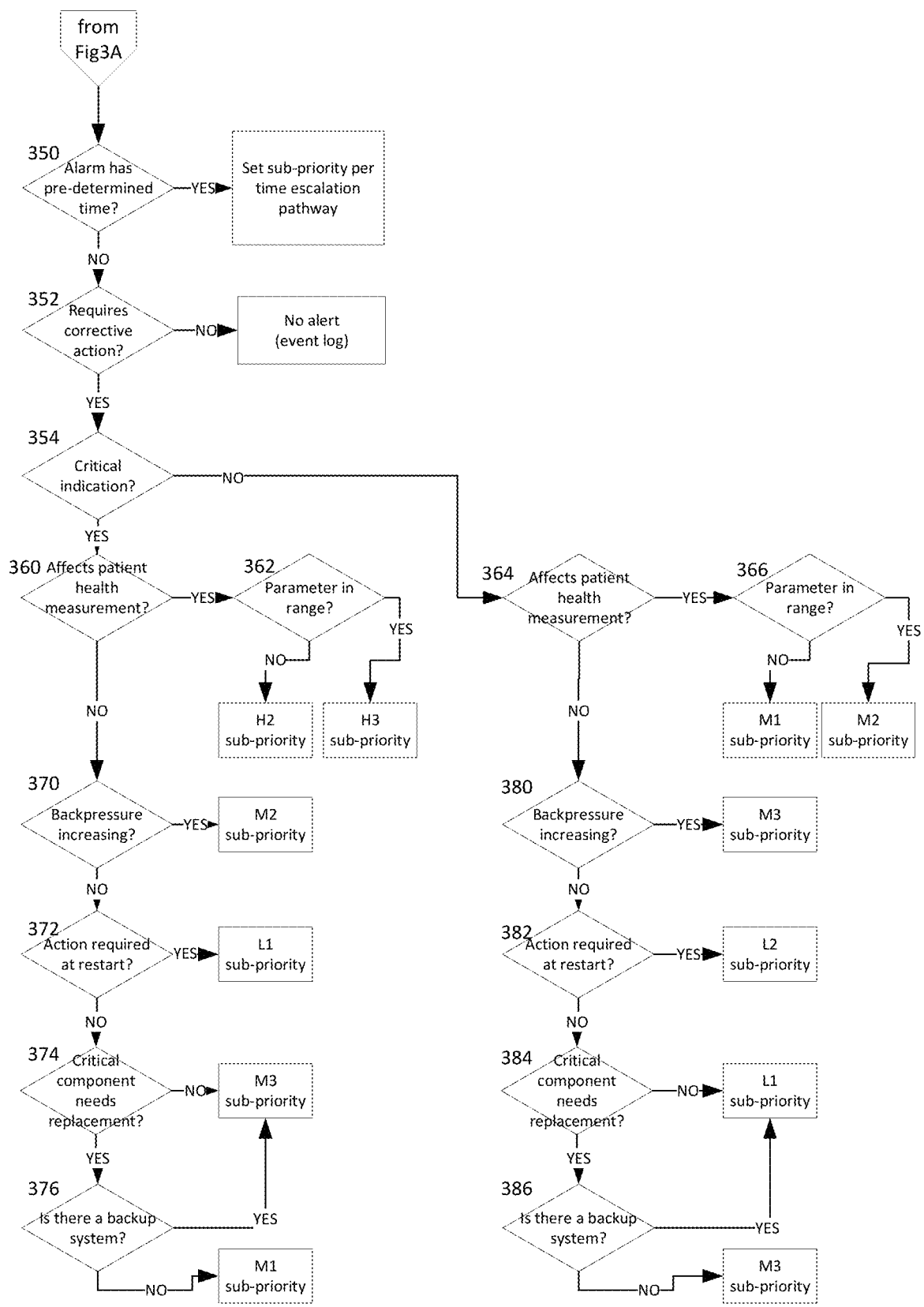

FIGS. 3A and 3B depict a flowchart 300 of an exemplary embodiment of a method of assigning a sub-priority to an alarm received from an infusion pump, according to certain aspects of the present disclosure. The process starts in FIG. 3A when an alarm is received from an infusion pump. The process branches in step 310 to FIG. 3B if the alarm is not associated with the pump being stopped or a condition that prevents an infusion from starting or continuing, otherwise proceeding to step 312.

Step 312 retrieves one or more of patient information, medication information, and device information for sources as described with respect to FIG. 1. Step 314 branches based on whether any of the medications are being administered to the patient with a critical indication for use or a non-critical indication for use.

In this example, the indication for use of the medication is the main factor that determines the initial priority category, e.g. H or M, for each alarm associated with an infusion pump. Medication or fluids with critical indications for use are high priority, e.g. H, and medications and fluids with non-critical indication for use are a lower priority, e.g. M. However, most medications have more than one indication for use and many medications have indications for use that are either critical or non-critical. For example, norepinephrine is used to treat acute hypotension, cardiac arrest or sepsis and they are all considered high critical indications for use, therefore any alarm associated with norepinephrine will be high priority, e.g. H1 or H2. On the other hand, hydrocortisone is high priority, e.g. H2, when used to treat status asthmaticus (severe acute asthma that requires immediate recognition and treatment) and medium priority, e.g. M2, when used to treat inflammation.

When a prescribed medication has multiple different indications for use, in certain embodiments, the Alarm Management Application 120 described in FIG. 1 will capture indication for use applicable to the patient from the EMR 142. In certain embodiments the application will retrieve this information from internal database 123. In certain embodiments, if there are several indications for use with different risk profiles, the Alarm Management Application 120 will prompt the clinician to choose which indication for use is associated with the prescribed medication or fluid.

Steps 320 and 324 each branch based on whether any of the medications are being administered to the patient are known to influence a patient health measurement such as a vital sign or lab value.

In certain embodiments, if the path branches from step 320 to step 322 for a medication or fluid with a critical indication of use, the process assigns a higher sub-priority, e.g. H2, if a vital sign or lab is out of a pre-determined range since the pump stoppage of this critical medication indicated to improve the patient health measurement would only worsen the situation. A lower sub-priority, e.g. H3 or M1, is assigned if the patient health measurement is within its respective pre-determined ranges.

For example, vasopressors are used to treat low blood pressure. If a vasopressor is infusing and the patient's blood pressure is being actively monitored, an alarm related to the vasopressor that occurs while the patient's blood pressure is below the acceptable range should be assigned a sub-priority, e.g. H2. If the blood pressure changes from below-range to within the acceptable range, then the sub-priority of that alarm may be reduced, e.g. H3. If the patient's blood pressure is above the acceptable range, then a lower sub-priority, e.g. M1 may be appropriate since the alarms associated with FIG. 3A are alarms that stop the therapy. In certain embodiments, if the blood pressure rises above an acceptable range and the vasopressor is still infusing then a high sub-priority alert is issued, e.g. H2 or H3, as shown in FIG. 3B. Lastly, if the patient being infused a vasopressor but the patient's blood pressure is not being actively monitored, then the sub-priority for any alarm related to the infusion of the vasopressor could be H1, H2 or H3 depending on the other dynamic attributes.

Medication and fluids may also be used to improve lab results. Lab values may start off normal and monitoring is ordered to ensure infusion of a medication or fluid does not change the lab result to an abnormal value. In other circumstances, the initial lab value may be outside the acceptable range and a medication or fluid is administered to improve it. For example, potassium IV may be administered to treat hypokalemia. An alarm related to the infusion of the potassium IV may be assigned an H2 sub-priority if the lab value is outside the acceptable range and assigned a lower sub-priority, e.g. H3 or M1, if the lab result is within the acceptable range.

Steps 330, 332, 334 are exemplary evaluations of PK/PD characteristics of a medication being administered to the patient. If any of the characteristics is of immediate concern, e.g. a short half-life, a loading dose, or a short onset period, the process assigns the highest sub-priority, e.g. H2. If all of the characteristics are not of immediate concern, e.g. a long half-life and a maintenance dose and a long onset period, the process assigns a lower sub-priority, e.g. H3.

In certain embodiments, Step 314 branches to Step 324 if the alarm is associated with a medication or fluid with a non-critical indication of use. If the path branches from step 324 to step 326, the process assigns a first sub-priority, e.g. M1, if a vital sign or lab is out of a pre-determined range and assigned a lower sub-priority, e.g. M2, if all vital signs and labs are within their respective pre-determined ranges.

Steps 340, 342, 344 replicate steps 330, 332, 334 in evaluating the PK/PD characteristics of a medication being administer to the patient for a medication with a non-critical indication for use. Steps 340, 342, 344 assign sub-priority M1 if any of the characteristics is of immediate concern and assign sub-priority M2 if all of the characteristics are not of immediate concern.

Picking up the process in FIG. 3B that branched from step 310 of FIG. 3A, step 350 checks whether the alarm is associated with a special time-related alarm, for example the battery alarm described with respect to Table 4. If associated with a battery alarm, then the sub-priority will be based on the amount of time remaining on the battery, otherwise step 352 checks whether the alarm is a notification that does not require correct action. Certain alarms do not require corrective action. For example, some infusion pumps have an internal mechanism that tries to self-correct an occlusion for 60-120 seconds. If the pump issues an alarm at the start of the self-correction process, the disclosed system waits in step 350 for the defined corrective period. If the pump correction is successful, the pump may issue an "alarm" that is simply a signal that the issue has been automatically resolved and then step 352 logs the event and terminates the process.

If the pump alarm is not associated with a time dependent alarm and a corrective action is required then the process continues to step 354 where it branches depending on whether the alarm is related to a critical indication of an administered medication. If a medication being administered has a critical indication for use, then step 354 branches to step 360 and further branches depending on whether the medication is known to have an effect on a patient health measurement such as a vital sign or laboratory test. In certain embodiments, if the path branches from step 360 to step 362, the process assigns a higher sub-priority, e.g. H2, if a vital sign or lab is out of a pre-determined range and assigned a lower sub-priority, e.g. H3 or M1, if all vital signs and labs are within their respective pre-determined ranges.

Steps 370, 372, 374 are exemplary evaluations of operational characteristics of the infusion pump being used to treat the patient. Each operational characteristic will have an associated criteria and an assigned sub-priority if that criterion is met. For an example of backpressure of an infusion line, an increasing backpressure is assigned an M2 sub-priority in step 370 while a constant backpressure (normal operation) will cause the process to branch to step 372 to consider other operational characteristics. In this example, if an action is required at restart of the pump, the process will assign an L1 sub-priority, otherwise proceed to step 374 that assigned an M1 priority if a critical component needs to be replaced and there is no back-up system and otherwise assigns a M3 priority.

In certain embodiments, if the path branches from step 354 to step 364 for a medication or fluid with a non-critical indication for use, the process assigns a first sub priority, e.g. M1, if a patient health measurement is out of a pre-determined range and assigned a lower sub priority, e.g. M2, if all patient health measurements are within their respective pre-determined ranges.

Steps 380, 382, 384 replicate steps 370, 372, 374 in evaluating the operational characteristics of the infusion pump being used to treat the patient with a medication or fluid with a non-critical indication for use. In general, the assigned priorities for each of the respective conditions will be lower when the medication or fluid is associated with a non-critical indication for use.

An example of a "routine" alarm is a near-end-of-infusion alarm from an infusion pump, which may indicate that there are 10 minutes remaining in the present infusion. The required corrective action is to obtain and connect a new IV bag, or a pre-filled syringe, of the medication to enable the next infusion to start. In certain embodiments, the initial sub-priority is set to a low level, e.g. M3, which will cause the system to notify a S3 clinician to retrieve the new IV bag and bring it to the patient's room. The alert to the S3 clinician may include the sub-priority, the necessary information to describe the item to be retrieved, e.g. the size of the IV bag and the medication concentration and volume. Even when the S3 staff member acknowledges the alert, the alarm is escalated to a higher priority, e.g. a M1, to notify the assigned S1 staff member to come to the patient room to connect the new IV bag and start the new infusion.

Multiple Infusions

A lot of patients that are hospitalized have multiple diagnoses that require infusions and often each diagnosis requires multiple infusions. In severe cases, patients may have 10 or more active infusions. For each separate infusion, the Alarm Management Application 120 will determine if the indication for use is critical or non-critical. In certain embodiments, the Alarm Management Application 120 will retrieve the indication for use from the database for each infusion. In certain embodiments, the application will determine the indication for use from the diagnoses that requires infusion from the EMR system 142. In certain embodiments, the Software Management App 120 will ask the clinician to identify the applicable indication for use if the medication has indications for use that are both critical and non-critical. In certain embodiments, the Alarm Management Application 120 will then determine if medications or fluids that have non-critical indications for use are codependent with medications or fluids that have critical indications for use. If yes, then the medication or fluid with the non-critical indications for use will take on the sub-priority alarm of the medication or fluid with the critical indication for use. For example, a patient who is hyperglycemic and receiving insulin, which has a critical indication for use, may be co-infused with low-concentration dextrose, which has a non-critical indication for use. In this situation, if an alarm occurs with the low-concentration dextrose solution, a sub-priority will be assigned using the rules defined for insulin.

Escalation and Silencing an Alarm

Figure 4:
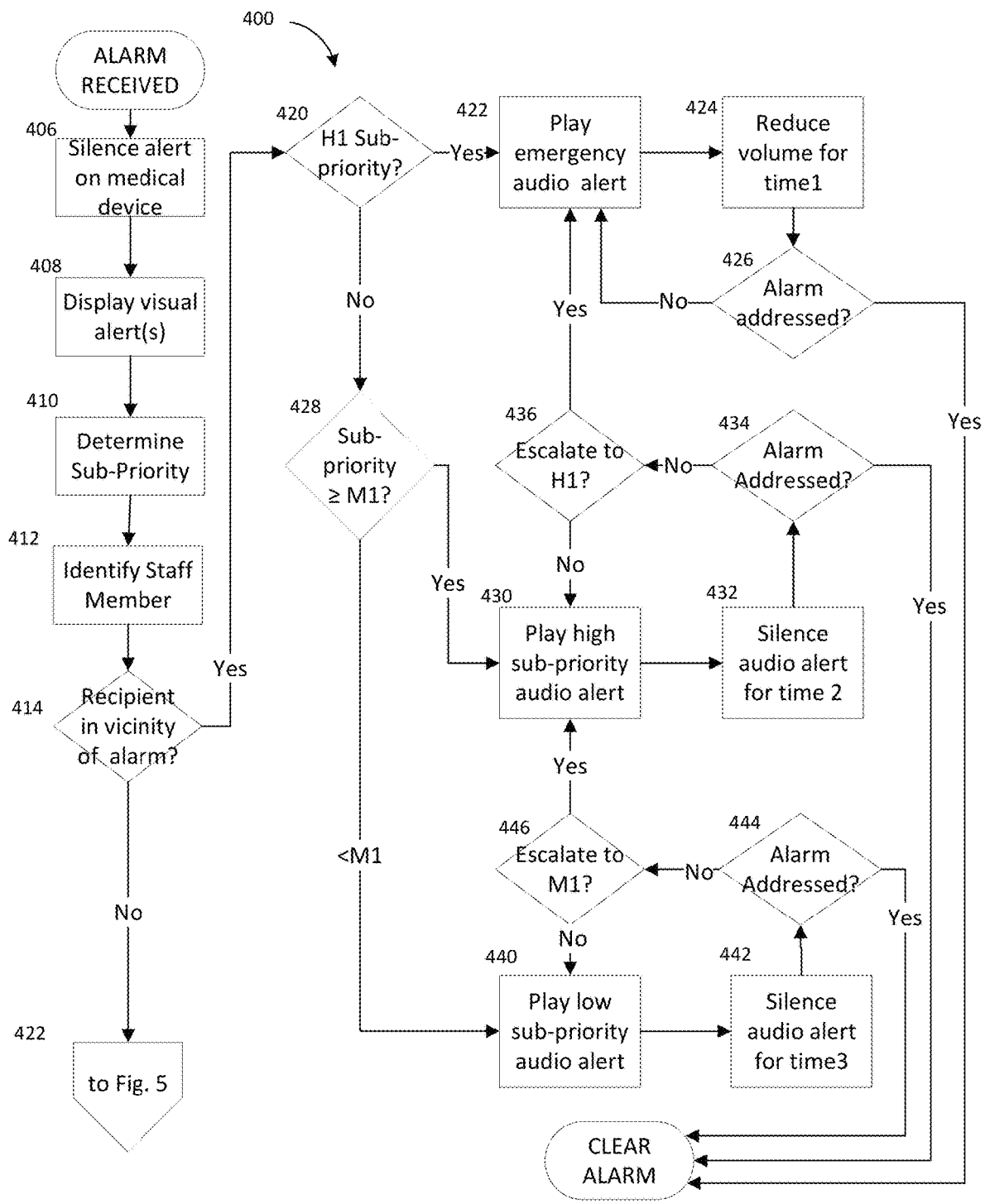
FIG. 4 is a flowchart of an exemplary embodiment of a method of silencing a bedside alarm, according to certain aspects of the present disclosure.

FIG. 4 is a flowchart 400 of an exemplary embodiment of a method of announcing and silencing a bedside alarm, according to certain aspects of the present disclosure. In certain embodiments, only the highest sub-priorities need to generate an audio alert.

The process starts with receipt of an alarm from a medical device located in the patient's room. In many cases, the medical device will emit an audible alert at the time of sending the alarm. The Alarm Management Application 120 sends commands to the medical device that issued the alarm in step 406 to silence the audio alert and to display the visual alert in step 408, which may also cause visual alerts to be displayed on the display 112 of the Alarm Management Application 120 and the personal devices of the intended recipients. In certain embodiments, a bidirectional protocol via a wired or wireless connection communicates the instructions to the device to silence its alarm. In other embodiments, the volume for the medical device may be turned to "off" or to its lowest setting and the audio alerts will be generated by the Alarm Management Application 120.

The alarm is assigned a sub-priority, for example using the process defined in FIGS. 6A-6E, in step 410 and the first staff member is identified in step 412. Step 414 determines whether the identified staff member is in the patient room, for example using information received from the RTLS system 162 of FIG. 1. If the staff member is not in the patient room, the process continues to FIG. 5. If the staff member is in the room, the process branches to step 420. Step 420 checks whether the present sub-priority is H1, in which case the process branches to step 422 to sound the emergency audio alert in the room. Note that in certain embodiments, steps 422, 430, and 440 include providing an alert to a staff member. In certain embodiments, if a clinician silences an H1 alarm, the volume of the alert is reduced for a certain amount of time "time1" in step 424 after which the process proceeds to step 426, which monitors the time elapsed since the alarm was received and determines whether the alarm has been resolved. If the alarm is resolved, the alarm is cleared, and the process is terminated. If time1 expires and the alarm is not resolved, the process returns to step 422 and repeats the emergency alert with a volume that matches or exceeds the original alert. In certain embodiments, an H1 sub-priority alarm cannot be silenced.

If the sub-priority was less than H1 in step 420, the process branches to step 428. If the sub-priority is greater than or equal to M1, the process branches to step 430, wherein the Alarm Management System 120 plays the "high" sub-priority alert. After a pre-determined amount of time elapses or if a clinician silences the alarm, the alert is silenced for a certain amount of time "time2" in step 432 after which the process proceeds to step 434 that monitors the time elapsed since the alarm was received and determines whether the alarm has been resolved. If the alarm is resolved, the alarm is cleared, and the process is terminated. If time2 expires and the alarm is not resolved, the process branches to Step 436 and determines if the alarm has escalated, for example per the workflow of FIG. 5, to an H1 sub-priority. If yes, then the process branches to Step 422, otherwise the process returns to step 430.

If the sub-priority was less than M1 in step 428, the process branches to step 440 that plays the "low" sub-priority alert. In certain embodiments, the low sub-priority audio alert may be silence and only a visual alert is provided in the room. After a pre-determined amount of time elapses or if a clinician silences the alarm, the alert is silenced for a certain amount of time "time3" in step 442 after which the process proceeds to step 444 that monitors the time elapsed since the alarm was received and determines whether the alarm has been resolved. If the alarm is resolved, the alarm is cleared, and the process is terminated. If time3 expires and the alarm is not resolved, the process returns to step 446, which escalates the sub-priority. If the sub-priority is now M1, the process branches to step 432 otherwise returns to step 440.

Table 8 provides an exemplary set of rules for whether an alarm is silenced or sounds in a patient room. In certain embodiments, only the highest sub-priority alarm sounds if it is known that no clinician is in the room. In certain embodiments, only the highest sub-priorities, e.g. H1, H2, and H3, play an audio alert as soon as the alarm condition occurs and the intended recipient is in the room. In other embodiments, the lower sub-priority alarms, e.g. M1-L3, only play an audio alert after a pre-defined delay when the alarm condition occurs and the intended recipient is in the room. In these situations, the visual alert associated with the alarm condition displays on the Alarm Management System's display 112 and the in the display of the device itself. In other embodiments, the hospital can configure which sub-priorities play an audio alert with a delay or without a delay as shown for the M1 sub-priority in Table 8.

TABLE 8

| Sub-priority | Escalation Times to Next Sub-Priority | Escalation Class | In-room Audio Alert When No Clinician in Room | In-room Audio Alert When Clinician is in Room |
|---|---|---|---|---|
| H1 | NA (highest) | highest | Yes | Yes (30 second delay) |
| H2 | 1 min | H1 | No | Yes |
| H3 | 2 min | H2 | No | Yes |
| M1 | 2 min | H3 | No | Yes/On a Defied Delay |
| M2 | 5 min | M1 | No | On a Defined Delay |
| M3 | 5 min | M2 | No | On a Defined Delay |
| L1 | 15 min | M3 | No | On a Defined Delay |
| L2 | 15 min | N/A | No | On a Defined Delay |

In this disclosure, silencing of medical device alarms takes a risk-based approach that considers the urgency of responding to alarm to prevent serious injury or death by determining what dynamic attributes of the patient are critical to consider. The consideration of the patient specific, device specific and time specific dynamic attributes provides the specificity that ensures only the alarms associated with the highest sub-priority, e.g. H1, need to have the audio component present at the bedside when a clinician is not in a room. All other alarms with lower sub-priorities may have their audible components turned off until they escalate to an H1 sub-priority.

Figure 5:
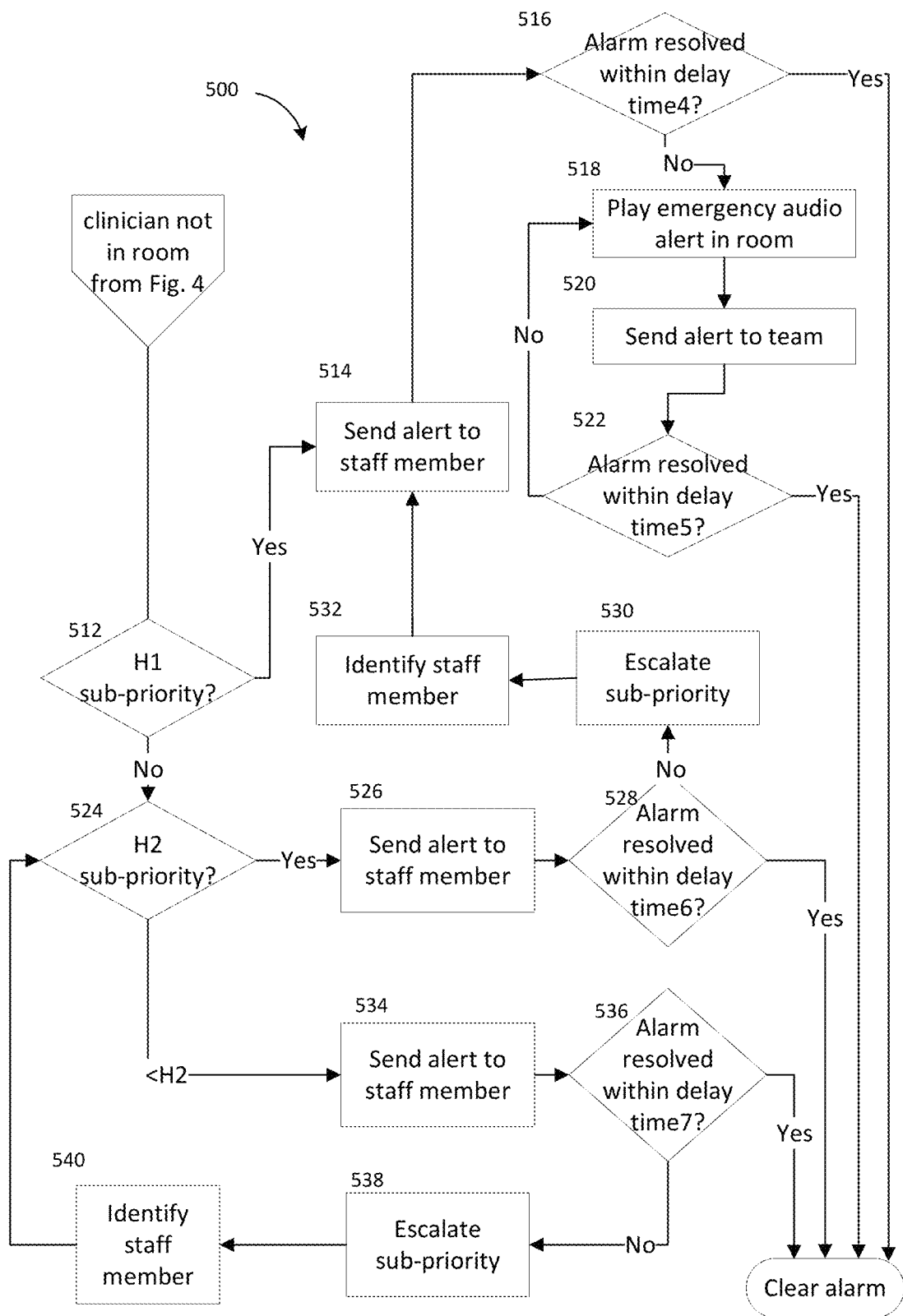
FIG. 5 is a flowchart of an exemplary embodiment of a method of escalating an alarm, according to certain aspects of the present disclosure.

FIG. 5 is a flowchart 500 of an exemplary embodiment of a method of escalating an alert in an alarm-forwarding scheme and playing an audio alert in the patient's room based on a risk threshold when a staff member is not in the room, according to certain aspects of the present disclosure.

The process starts with step 512, a continuation from FIG. 4 after the alert is sent from the Alarm Management Application 120 to a remote staff member's personal device. If the assigned sub-priority is H1, step 512 branches to step 514 that sends an alert to the identified staff member assigned to the patient for an H1 sub-priority. Step 516 determines if the alarm is resolved in a defined amount of time 4 and if not plays an emergency audio alert in the patient's room in Step 518 and sends the alert in step 520 to the entire clinician team on the floor or assigned to the patient. In certain embodiments, only a sub-priority of H3 or higher when escalated to an H1 sub-priority will play the emergency audio alert in the patient's room when no clinician is available. Step 522 determines if the alarm is resolved in delay time 5, and if not, it continues to generate the emergency audio alert in step 518. In some embodiments, the volume of the emergency audio alert increases to its maximum volume. If the alarm is resolved within delay time 4 instep 516, or delay time 5 in step 522, then the alarm is cleared.

If the assigned sub-priority is not H1, then the process proceeds to step 524. If the assigned sub-priority is H2, step 524 branches to step 526 that sends an alert to the staff member assigned to the staff role associated with the present sub-priority and proceeds to step 528. In step 528, the software determines if the alarm has been resolved within the specified delay time. If the alarm is resolved, step 528 clears the alarm, and the process is terminated. If time 6 expires and the alarm is not resolved, the process branches to step 530, wherein the sub-priority is escalated to H1 and the process proceeds to step 532 where the Alarm Management Application 120 identifies the staff member. In certain embodiments this staff member is the same person who received the H2 sub-priority alert. In other embodiments, it is a new staff member, e.g. back-up clinician. Once the staff member is identified the H1 sub-priority is conveyed on the staff member's personal device at Step 514 and the steps for the H1 sub-priority process are completed.

If the sub-priority is initially less than H2, then an alert is sent to the identified staff member in step 534. If the alarm is resolved within time 7, step 540 clears the alarm and the process is terminated. If time 7 expires and the alarm is not resolved, the process branches to step 538, wherein the sub-priority is escalated. Step 540 identifies a staff member either the same staff member or a new staff member. The escalation process returns to step 524, where the software determines if this is a H2 sub-priority.

The present disclosure describes a system and method for reducing alarm fatigue which entails reducing the number of alerts a staff member receives on their personal device. Steps 514, 526, and 534 send alerts to staff member's personal devices. In certain embodiments, sending an alert means updating the sub-priority on the same staff member's personal device without receiving a new alert from Alarm Management Application 120. The personal device will have the escalation times for each sub-priority stored in its local memory. In some embodiments, the escalated alert is accompanied by a vibration or beep to notify the staff member of the escalation.

Alarm fatigue is often exacerbated when more than one device is alarming concurrently in a patient's room with or without a clinician present. In the current disclosure, the alarm management device as described in FIG. 1, e.g. an alarm management device present in patient's room with a user interface and speaker, handles concurrent alarms. The alarm management software defines sub-priorities based on dynamic attributes for each device that alarms in the room. In certain embodiments, only H1 alarms generate audio in the room. For example, if an infusion pump has an H1 alarm while a ventilator has an M1 alarm, the alarm management device will generate an audio emergency alert and visually display device identification information associated with the pump that is alarming. The display of the ventilator alarm sub-priority would occur underneath the infusion pump sub-priority signaling lesser importance. In certain embodiments, the audio alert will have a device specific melody associated with an infusion pump which a clinician will recognize as an infusion pump alarm. In other embodiments, the alarm management software will instruct the infusion pump to generate the audio signal.

In some situations, e.g. ICU, multiple devices are alarming, and each device has an associated H1 as the original sub-priority. In certain embodiments, the alarm management device will generate an audio emergency alert and visually display the alarms in order of importance.

In some situations, multiple devices are alarming with H1 sub-priority alarms, however one device has the H1 sub-priority as the original sub-priority, while the other device has escalated to an H1 priority alarm after a defined period of time, e.g. an H3 sub-priority escalates to an H1 alarm. In certain embodiments, the device associated with the original H1 sub-priority alarm will be the alarm that generates the audio signal, e.g. a device specific audio signal, and visually displayed first, e.g. on the alarm management device user interface. In this situation, the original H1 sub-priority alarm is the true life-threatening situation.

Ventilator Alarms

In certain embodiments of the present disclosure, the sub-priority of a ventilator alarm may increase or decrease from the baseline value based on dynamic attributes from the patient, e.g. underlying condition, from the device, e.g. an $O_2$ setting on the device, or based on time, e.g. the time to retrieve a new ventilator after a system error, verifying a new sensor, etc. Often, ventilators have more than one clinical alarm simultaneously triggering based on the patient's ventilation status. For example, high airway pressure alarms are often associated with low tidal volume or low minute volume since the patient gets little or no ventilation when a high-pressure alarm has triggered. In certain embodiments, the presence of a second distinct clinical alarm following a first one indicates disease progression or worsening of a patient's ventilation status and the sub-priority of the first alarm will increase to reflect this.

FIGS. 6A-6E depict a flowchart 300 of an exemplary embodiment of a method of determining an initial alarm sub-priority to an alarm received from a ventilator, according to certain aspects of the present disclosure.

Figure 6A:
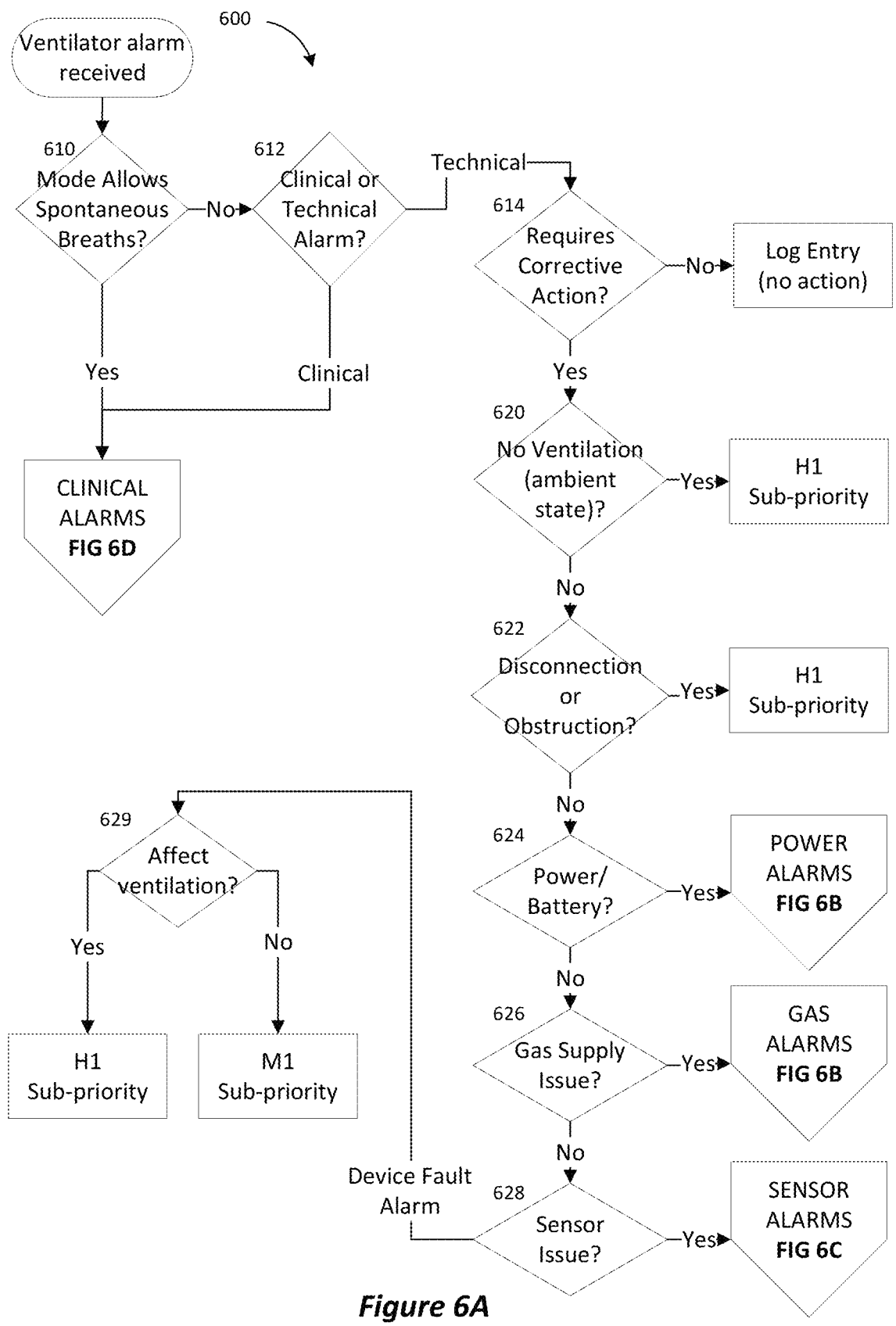
FIGS. 6A-6E depict a flowchart of an exemplary embodiment of a method of determining an initial alarm sub-priority to an alarm received from a ventilator, according to certain aspects of the present disclosure.

The process starts in FIG. 6A with receipt of a ventilator alarm. Step 610 branches depending on whether the ventilator is operating in a mode that allows spontaneous breaths by the patient or if patient is passively breathing and relying solely on the ventilator for breathing. The process branches from step 610 to FIG. 6D if the patient cannot spontaneously breath and from step 612 to FIG. 6D if the alarm is a clinical alarm. In this example, the workflow for assigning sub-priorities to ventilators contain logic for passive breathers, however, for spontaneous breathers, the sub-priorities will be lower since the harm associated with not responding to an alarm in a timely fashion is lessened.

At Step 612, the software branches on whether the alarm is a clinical alarm or a technical alarm. If a technical alarm, step 614 determines if the alarm is not actionable, i.e. for information only, and logs this information and terminates these processes. In certain embodiments, the highest sub-priority alarm, e.g. H1, is reserved for technical alarms that put the ventilator in an ambient state, i.e. state of no ventilation, and conditions that seriously compromise the ventilation circuit, e.g. disconnection or obstruction. Steps 620 and 622 check for these conditions and assign an H1 sub-priority. Power and gas supply alarms branch to FIG. 6B in steps 624, 626. Sensor alarms branch to FIG. 6C in step 628. In Step 629, a system error or device fault alarm that affects ventilation will be assigned a higher sub-priority, e.g. H1 or H2 sub-priority alarm. If ventilation is not affected, e.g. the display screen is not available, the alarm will be assigned a lower sub-priority, e.g. M1 or M2 sub-priority.

Figure 6B:
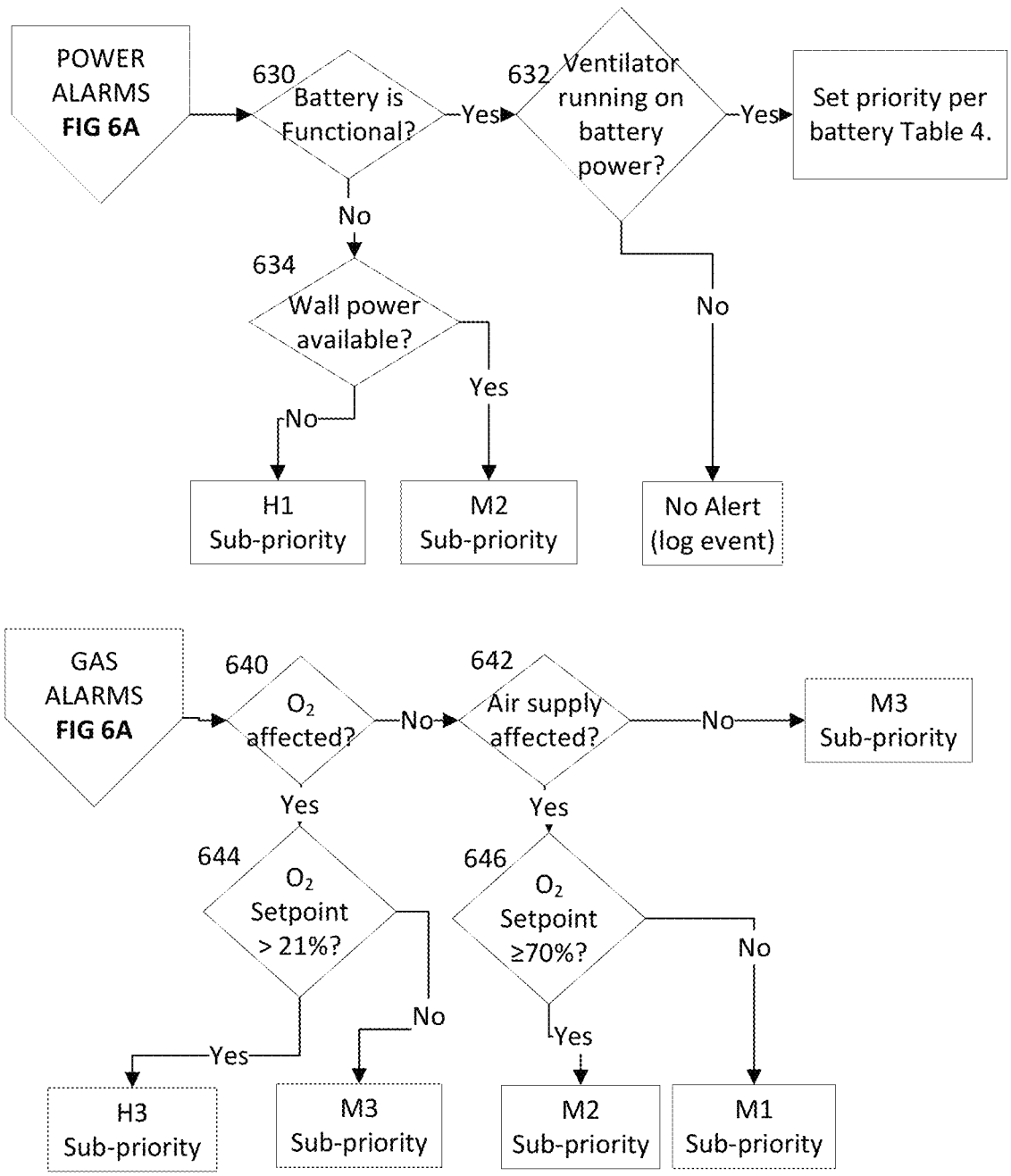

FIG. 6B depicts exemplary process for handling power and gas alarms. For power alarms, step 630 determines if the battery is functional. If the battery is operational, then the step 632 determines whether the ventilator is running on wall power or batteries. If the ventilator is running on wall power, and the battery is functional, then no alert is assigned since this may be just an alarm to say a battery with low power is recharging. If the ventilator is running on battery power, then a sub-priority will be defined based on the amount of time left on the battery. For example, an alarm indicating there is ten minutes of battery power will be assigned a M2 sub-priority.

If the battery is not functional, e.g. a charging issue, then step 634 determines whether the ventilator is running on wall power. If the battery is non-operational and the ventilator has lost its connection to wall source, then the ventilator has turned off and Step 634 assigns the highest sub-priority, e.g. H1. If the battery is not functional or has lost its ability to charge and the ventilator is connected to a mains power source is not, then step 634 assigns a lower sub-priority, e.g. M2 sub-priority. Depending on the staff role associated with a ventilator M2 priority, a lower-level staff member can install a new battery.

For gas alarms, step 640 determines whether the alarm is associated with an oxygen supply issue, e.g. a supply of $O_2$ has stopped. Room air consists of 21% oxygen. Patients may receive supplemental oxygen at levels up to 100% oxygen. Step 644 branches based on whether a patient is receiving room air or receiving supplemental oxygen. In certain embodiments, if the patient is receiving supplemental oxygen, a higher sub-priority is generated, e.g. H3, since the alarm indicates that the patient may be receiving less than the intended amount of oxygen. In other embodiments, the sub-priority is defined based on the amount of $O_2$ that is required. If the patient is receiving only room air or very minimal supplement oxygen, then a lower sub-priority is assigned, e.g. M3.

Ventilators can provide a breathing mixture from gases other than pure oxygen, e.g. manufactured air or heliox. If an air or heliox Gas Supply alarm is received, then the patient may be receiving pure oxygen from the ventilator. Too much oxygen in the breathing mixture for an extended period of time may damage lung tissue. In certain embodiments, if step 642 determines that the alarm is related to the patient receiving the breathing mixture and the patient is breathing a 70% or greater oxygen levels, then step 646 assigns a lower sub-priority, e.g. M2. If the oxygen content of the breathing mixture is set to <70% oxygen, then step 646 assigns a higher sub-priority, e.g. M1, since the patient may not tolerate the excess oxygen. If the alarm is related to other aspects of the gas supply, for example a low gas supply tank pressure alarm, then step 642 assigns a lower sub-priority alarm, e.g. M3.

Figure 6C:
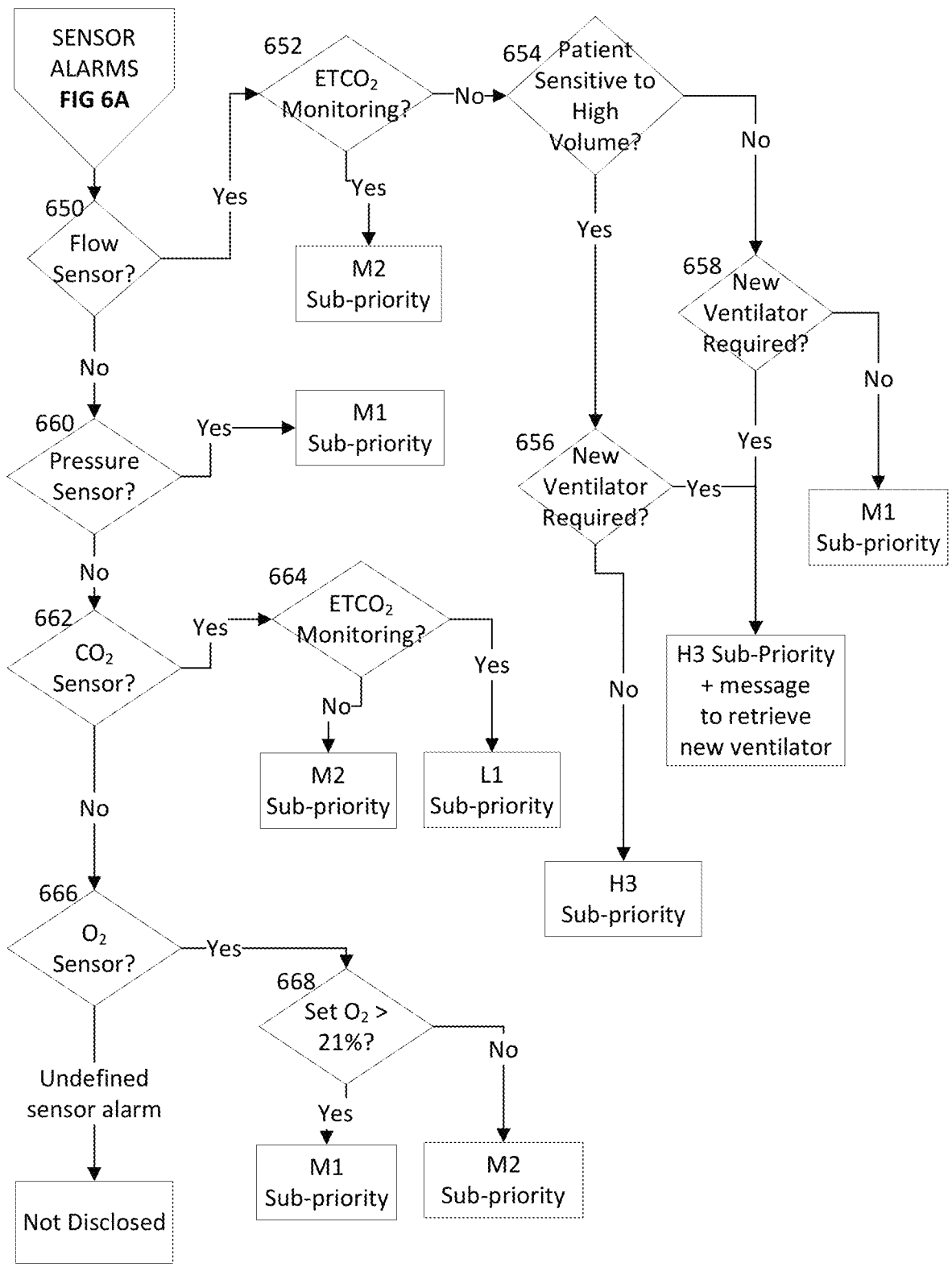

FIG. 6C provides the logic for assigning sub-priorities to sensor alarms, which can be related to non-functional sensors, sensors hooked up incorrectly, sensors requiring calibration, etc. Ventilators typically have flow, pressure, oxygen ($O_2$), and carbon dioxide ($CO_2$) sensors. The flow sensor is the most important sensor to maintain during the ventilation to determine if the patient is getting the correct flow rate. Alarm sub-priorities will be decreased if a primary sensor, e.g. flow sensor or $CO_2$ sensor, stops working but a redundant external monitoring activity is concurrently operating. For example, a lower sub-priority is warranted for both non-functional flow sensors and $CO_2$ sensors when the patient is also being monitored by an $ETCO_2$ monitor.

Steps 650, 660, 662, 666 branch depending on the type of sensor associated with the alarm. For flow sensor alarms, step 650 branches to step 652 where the application determines if there is a redundant monitoring source, e.g. $ETCO_2$ monitoring, and assigns a M2 sub-priority. If there is no redundant monitoring source then the software branches to step 654. If the patient is sensitive to excessive tidal volume, e.g. patient with an underlying condition of ARDS, COPD, etc., the process branches to step 656 that determines whether a new ventilator is required. If a new ventilator is not required, a H3 sub-priority is assigned. If a new ventilator is required, some manufacturer's flow sensors require a lengthy replacement and testing process, which requires manual ventilation in the interim, and an H3 sub-priority is assigned with an additional alert to a second staff member to retrieve a new ventilator.

If the patient is not sensitive to excessive tidal volume, then the software branches to step 658 to determine if a new ventilator is needed. If a new ventilator is needed an H3 sub-priority is assigned with an instruction to retrieve a new ventilator. Otherwise, a M1 sub-priority is assigned.

In the example of FIG. 6C, any pressure sensor alarm is assigned the same sub-priority, e.g. M1, in step 660.

In FIG. 6C, a $CO_2$ sensor alarm is assigned a sub-priority, e.g. M2, in step 664 if there is no $ETCO_2$ monitoring and a lower sub-priority, e.g. L1, if there is $ETCO_2$ monitoring.

After branching at step 666, an 02 sensor alarm is assigned a sub-priority, e.g. M1, in step 668 if the patient is receiving supplemental oxygen and a lower sub-priority, e.g. M2, if the patient is not being treated with supplemental oxygen.

Figure 6D:
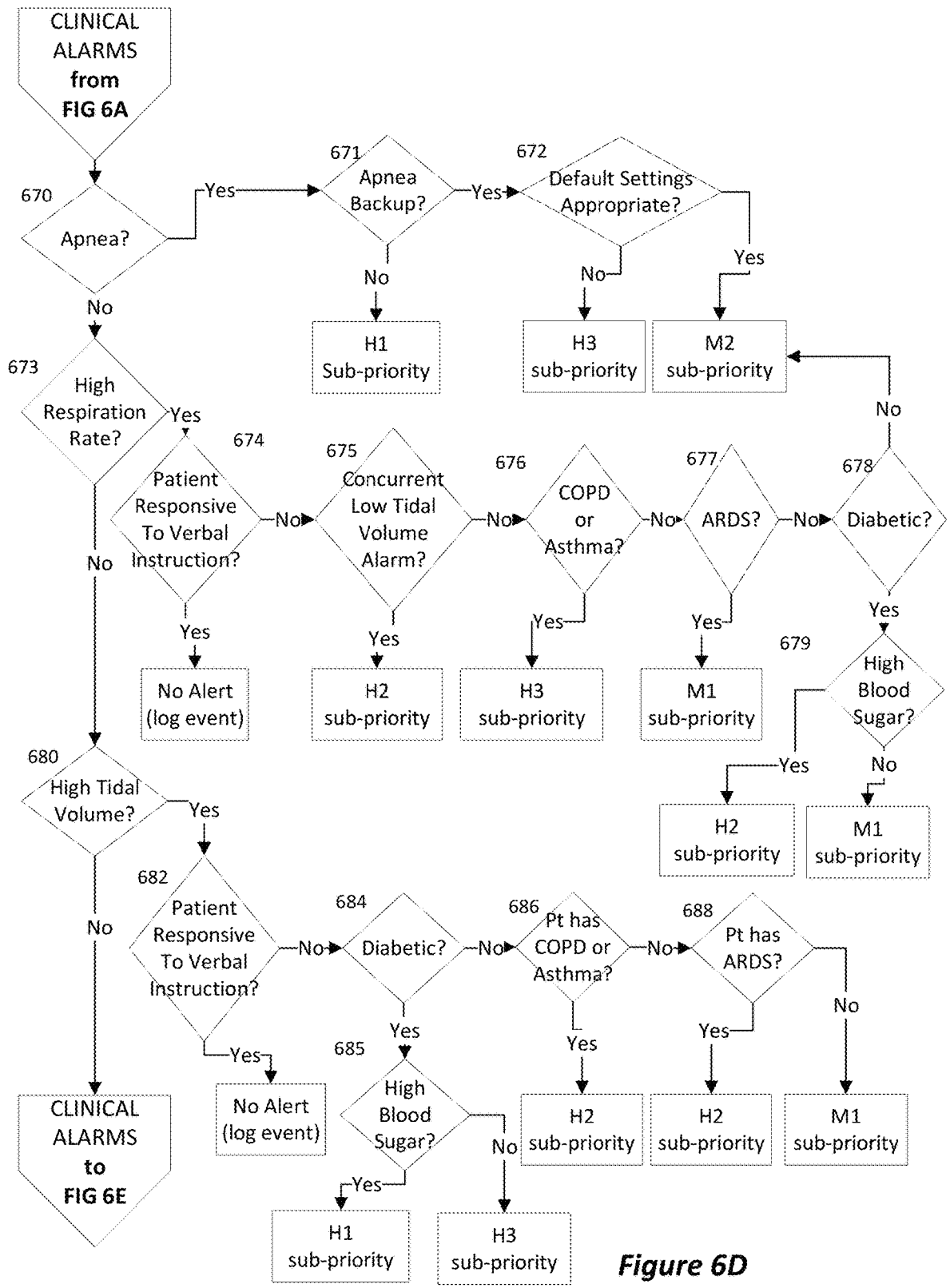
Figure 6E:
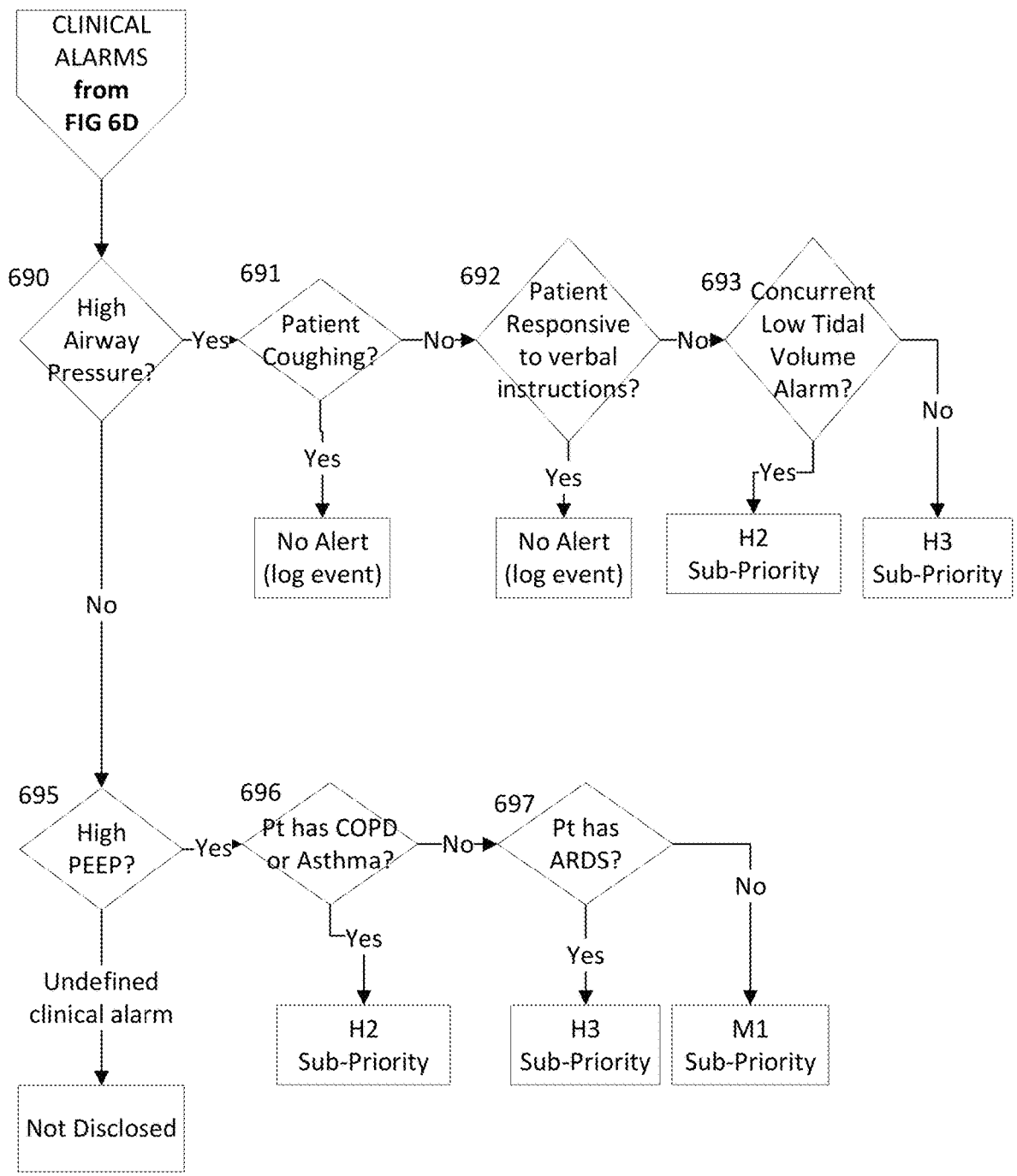

FIGS. 6D and 6E show the methodology of assigning a sub-priority for clinical alarms. These figures do not represent an exhaustive list of clinical alarms but cover numerous examples of how dynamic attributes define a sub-priority for a ventilator clinical alarm. Some of the steps in these figures illustrate how an alarm sub-priority may change from its baseline value based on the patient's medical or current condition e.g. COPD, a patient action e.g. coughing, or a redundant mechanism to mitigate harm e.g. $ETCO_2$ monitoring. Patients with certain types of underlying conditions require protective strategies while being treated with a ventilator. Conventional systems rely on the clinician to manually adjust the settings of the ventilator based on the underlying conditions. It is important that patients who have underlying conditions in need of a protective strategy have a higher sub-priority, so clinicians respond quicker to mitigate the potential increased harm. Alternatively, patients who may not need protective strategies may have lower sub-priorities which allows clinicians more time to respond and reduces alarm fatigue.

The disclosed method enables a hospital to define a set of rules that modify the sub-priorities assigned to certain alarm conditions that may interact with the underlying conditions. For example, patients who have COPD or asthma may experience chronic inflammation of small airways, which increases airway resistance and decreases elastic recoil. This leads to limited airflow and an impaired ability of the airways to remain open at the end of breath expiration. The collapse of airways at the end of expiration results in incomplete expiration, higher residual end-expiratory volume, hyperinflation, and auto-high positive end-expiratory pressure (auto-PEEP). Protective measures for ventilating COPD and asthma patients include preventing air trapping in the smaller airways by reducing the tidal volume, ensuring respirations are slow and deep, and ensuring the expiration time is significantly long enough to remove air.

In certain embodiments, higher sub-priorities are defined for diabetics. Diabetics who are prone to developing high blood sugar and potentially diabetes ketoacidosis (DKA) rely on respiratory mechanisms to compensate for metabolic acidosis and, therefore, are at a higher risk for certain alarm conditions which may indicate disease progression.

Step 670 covers an apnea alarm or when the ventilator is set to allow the patient to breathe by themselves, i.e. spontaneous breathing, however there is no respiration detected. Step 671 assigns the highest sub-priority, e.g. H1, if there is no back-up ventilation, otherwise branches to step 672 that assigns a lower sub-priority, e.g. M2, if the default settings of the back-up ventilation are appropriate for the patient and an intermediate sub-priority, e.g. H3, if the back-up setting are not appropriate.

Steps 673 and 680 branch for a high respiration rate and high tidal volume, respectively. For certain clinical alarms, the patient may be fighting the ventilator's breathing pattern due to agitation or pain. It may be possible to coach the patient to modify their behavior, e.g. their rate of breathing or their depth of inhalation, if the patient is not completely sedated. Coaching may include the instructions of Table 9. If the patient is responsive to verbal instructions, provided either in-person or remotely, e.g. via video terminal or speaker, then steps 674, 682 branch and the coaching successfully changes the patient's breathing pattern to address the alarm condition, then no alarm is generated. If the coaching is unsuccessful, then the process reverts to the alternate path from these steps and branches to steps 675, 684 respectively.

TABLE 9

| Alarm | Cause | Coaching |
|---|---|---|
| high airway pressure | asynchrony | match ventilator setting for respiration rate |
| fast respiration rate | agitation, anxiety | slow respiration rate |
| high tidal volume | agitation, anxiety | take shallower breaths |

If the high respiratory rate alarm is associated with a concurrent low tidal alarm indicating a worsening ventilation status of patient, step 675 assigns a high sub-priority, e.g. H2. If there is no concurrent alarm and the patient has COPD or asthma, then step 676 in this example assigns the same priority, e.g. H3, since a fast rate may affect the patient's breath expiration and lead to air stacking in patient's having smaller airways. If the patient's underlying medical condition is acute respiratory distress syndrome (ARDS), then step 677 assigned a lower sub-priority, e.g. M1. If there is no concurrent alarm and the patient does not have COPD, asthma, or ARDS but is diagnosed as diabetic, step 679 checks the latest lab test and assigns a higher sub-priority, e.g. H2, if the patient has high blood sugar since the high respiration rate may indicate patient deterioration in this situation. If the diabetic does not have high blood sugar, then a lower sub-priority, e.g. M1, is assigned. In this example, the default for a respiratory alarm is an M2 sub-priority.

For a high tidal volume alarm, the patient is assessed in steps 684, 686, 688 for diabetes, COPD or asthma, and ARDS and appropriate sub-priorities are assigned. These sub-priorities are typically higher than sub-priorities for similar patient underlying conditions for a high respiration rate alarm because the high tidal volume usually occurs after a high respiration rate and/or indicates greater disease progression. A diagnosis of diabetes and a laboratory test showing high blood sugar causes step 685 to assign a high priority, e.g. H1, since the metabolic alkalosis is at a more advanced stage. Meanwhile normal blood sugar and the other conditions result in lower-level sub-priorities, H2 or H3. In this example, the default for a tidal volume alarm is an M1 sub-priority.

FIG. 6E depicts an exemplary process for two clinical pressure alarms. After branching in step 690 for a high airway pressure alarm, step 691 determines whether the patient is coughing, for example by checking for the sound of coughing prior to, during, or after the time of the alarm using a microphone near the patient, as it is common for this type of alarm to be triggered when the patient is coughing. In certain embodiments, microphone 114 of FIG. 1 is used to detect coughing. If the alarm unit microphone determines coughing is the reason for the alarm, then the event is logged, and no alarm is sent. If the patient is responsive to verbal instructions (See Table 8), to try to match the ventilation respiration settings and not fight the ventilation as seen in patient ventilator asynchrony then step 692 will provide coaching and suppress the if the instruction successfully resolves the high airway pressure alarm condition. If the coaching is unsuccessful, the process reverts to the alternate path and branch to step 693. If the high airway pressure alarm is associated with a concurrent low tidal alarm, step 693 assigns a high sub-priority, e.g. H2, otherwise the default sub-priority, e.g. H3, is assigned.

After branching in step 695 for a high positive end-expiratory pressure (PEEP) alarm, step 695 checks whether the patient has COPD or asthma and, if so, assigns a high sub-priority, e.g. H2, because high PEEP can cause injury with COPD or asthma patients. If the patient does not have COPD or asthma but is diagnosed as having ARDS, then a slightly lower sub-priority, e.g. H3, is assigned. In this example, the default for a high PEEP alarm is to assign an M1 sub-priority.

The disclosed system also provides an ability to adjust the threshold values for triggering a clinical alarm based on underlying conditions. For example, patients with ARDS may require a lower tidal volume alarm threshold and/or a lower PEEP alarm threshold. In addition, alarms for high tidal volume or PEEP for ARDS patients requires a quicker response time for clinicians to address the alarm condition before potential patient harm occurs. In both cases, the assigned sub-priority of certain alarms is increased for patients with the underlying condition compared to the same alarms for patients without these conditions.

Figure 7:
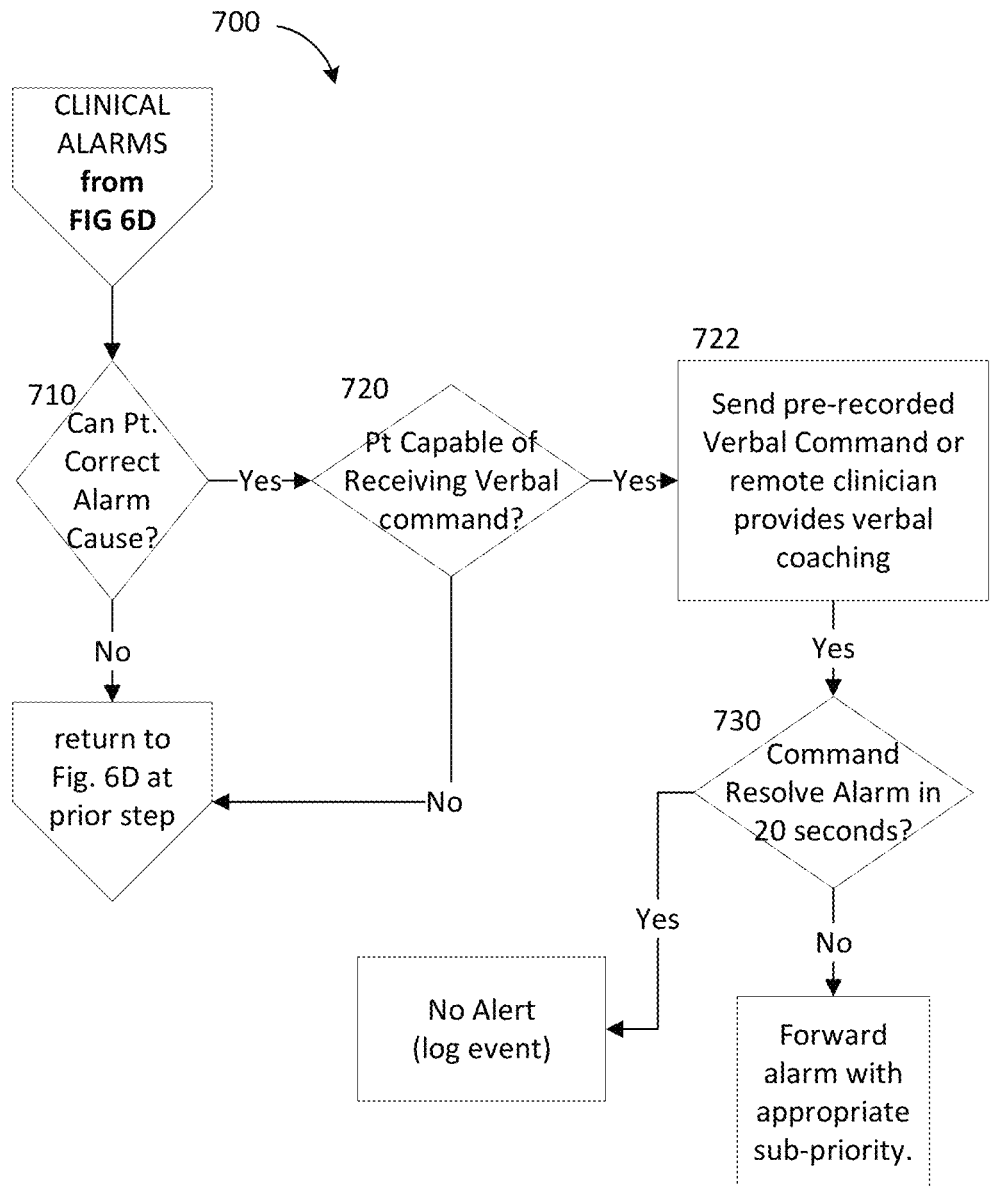
FIG. 7 is a flowchart of an exemplary embodiment of a method of guiding a patient to resolve a ventilator alarm, according to certain aspects of the present disclosure.

FIG. 7 is a flowchart 700 of an exemplary embodiment of a method of guiding a patient to resolve a ventilator alarm, according to certain aspects of the present disclosure. This process starts when an alarm condition has been received and Step 10 determines from the information in the alarms databased that one of the causes of the alarm may be resolved by a patient modifying their breathing pattern. If one of the causes of the alarm may be resolved by a patient modification, then Step 710 branches to step 720 otherwise it branches to the next decision point for the specific alarm. Step 720 determines whether the patient is capable of responding to verbal commands, e.g. is the patient conscious or sedated, and also returns to the next decision point for the specific alarm if the patient is unable to respond. If the patient is able to respond, the system provides coaching to the patient in step 722, either with a pre-recorded verbal command or via a staff member speaking through a remote interface via a video display or speaker. If the alarm condition is resolved within a pre-determined time period, then step 730 clears the alarm and logs the event. If the patient is unable to resolve the alarm condition, an appropriate sub-priority is assigned and an alert sent to the associated staff member.

Alarm Suppression

There are certain ventilator alarms where the potential cause of the alarm is related to a patient's behavior, e.g. agitation or anxiety. For example, a high respiratory rate or a high tidal volume, e.g. fast and/or shallow breathing, may generate an alarm reflects agitation of a patient being on a ventilator in a hospital room by themselves when they are awake, lightly sedated or on a daily spontaneous breathing trial. In addition, a patient may be fighting the respiration pattern provided by the ventilator, a behavior known as "patient-ventilator asynchrony," which may result in several alarms, e.g. high airway pressure alarm. For these alarms, it is possible to coach a patient who is capable of following instructions to change their breathing pattern, e.g. slow down respiration, to resolve the alarm. In certain embodiments, the disclosed system can resolve these alarms without involvement of a staff member.

For example, the Alarm Management System 120 receives a ventilator alarm and determines from a database in its memory that the alarm might be related to a patient's breathing pattern and that may be corrected with instruction, e.g. verbal command. The Alarm Management Application 120 can retrieve the ventilation mode and the set-point and actual respiratory rates from the ventilator and determine if the mode supports spontaneous breathing and if the patient is breathing spontaneous breaths. If both conditions are met, then in certain embodiments the alarm unit will retrieve the audio/video file from the database in its memory and provide the pre-recorded instructions on a video or audio device. In certain embodiments, a remote staff member may provide instructions via an audio or visual device. In certain embodiments, a pre-determined time period, e.g. twenty seconds, is allowed for the patient to be coached to resolve the alarm. If successful, then the alarm clears, and an information alert is sent to a remote clinician. If the time expires or the Alarm Unit determines that a potential cause of the alarm is not associated with patient behavior or the patient is not capable of responding to instructions, then the Alarm Management System 120 software will continue to process the alarm and assign an appropriate sub-priority alarm. In certain embodiments, the Alarm Management System 120 considers the time spent on this instruction when defining the sub-priority.

In another embodiment, the Alarm Unit 110 uses its microphone to determine if the patient is coughing, which may be the reason for a high airway pressure alarm. The Alarm Unit's memory database will know that a potential cause of high airway pressure alarms is a patient coughing. In certain embodiments, the alarm unit hardware includes a built-in microphone (114 of FIG. 1) that can detect that a patient is coughing during a high airway alarm. If confirmatory, then a high airway pressure alarm will not be forwarded to a remote clinician if it does not continue after the coughing ceases. If the patient is not coughing, then then the software alarm logic for high airway pressure alarms will continue to proceed through its logic as shown in FIG. 6E.

Patient Monitor Alarms

A patient monitor is used to monitor a patient's vital signs and detect arrhythmias of different criticality, e.g. life-threatening, critical, and non-critical. Monitors are ubiquitous in both high acuity hospital environments, e.g. ICU, and lower acuity environments, e.g. medical/surgical floors. They play a significant role in generating the number of alarms in these environments and a large percentage of these alarms are not actionable, e.g. false positive alarms. The high frequency of non-actionable monitor alarms may have many causes, e.g. a weak signal to noise ratio, a motion artefact, electromagnetic interference, etc. To combat alarm fatigue, it is vital that dynamic attributes are used to provide context to alarms so clinicians know which alarms may be actionable and the sense of urgency in responding to them.

When clinicians respond repeatedly to monitor alarms that do not require an actionable response, they are inclined to take longer to respond to subsequent alarms, or resort to unsafe practices, e.g. turning off the volume of a monitor or utilizing the monitor's ability to suppress future alarms. Numerous safety signals from public databases indicate that turning off the alarm volume or using the suppression feature of a monitor is unsafe and may lead to serious injury or death. To facilitate preventing alarm fatigue and to ensure critical alarms are responded to in a timely fashion, the embodiments in this application clarify how dynamic attributes are used to provide the necessary alarm specificity to achieve these goals. Dynamic attributes provide context to clinicians to facilitate determining when a monitor alarm is associated with a true critical event, when a more urgent response is required to address an alarm associated with lack of monitoring or reliability of monitoring, and when a reduced sub-priority requiring a less urgent response is required, reducing the alarm fatigue factor for clinicians.

Figure 8A:
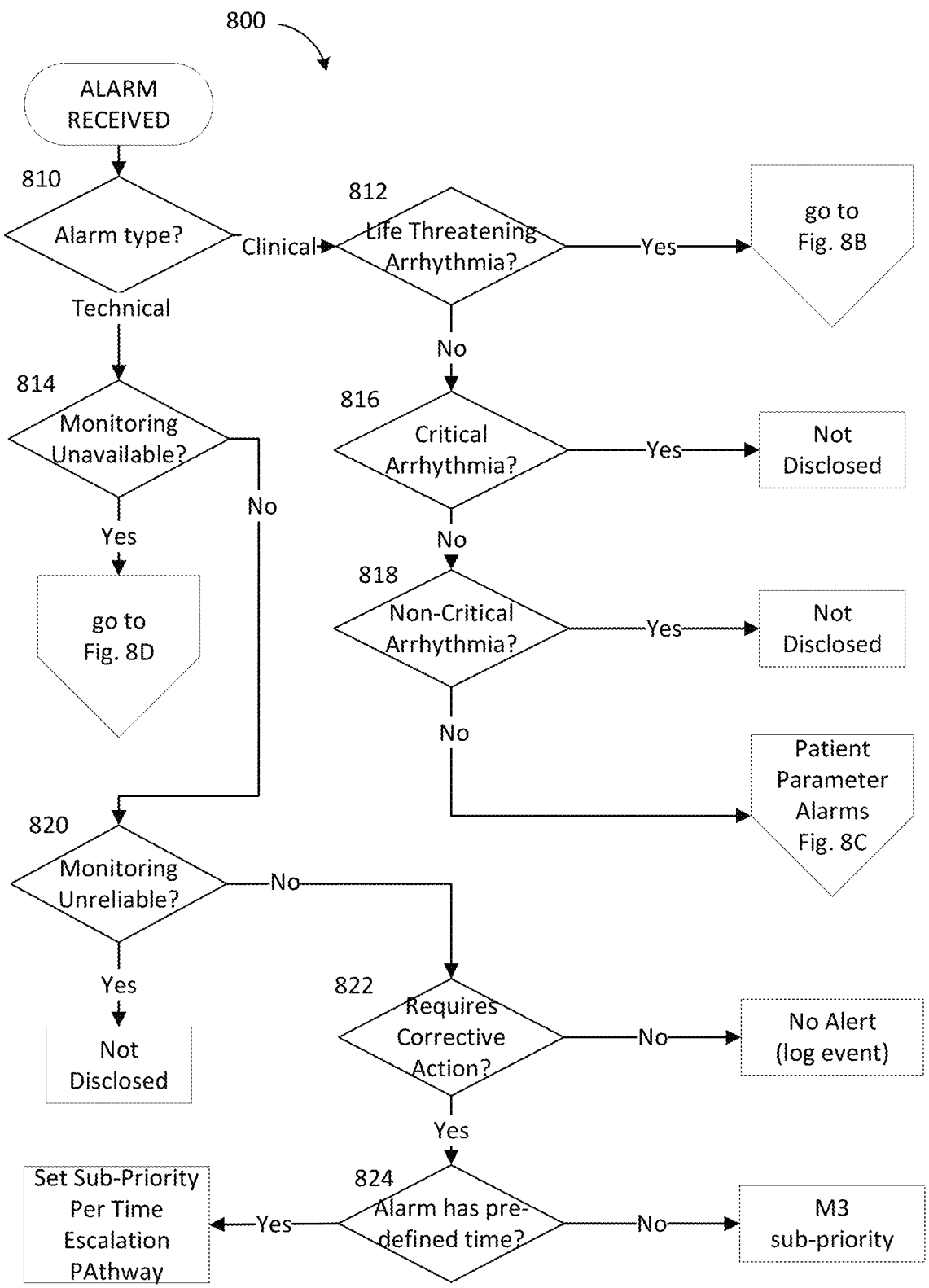
FIGS. 8A-8D depict a flowchart of an exemplary embodiment of a method of handling an alarm received from a monitoring device alarm, according to certain aspects of the present disclosure.

FIGS. 8A-8D depict a flowchart of an exemplary embodiment of a method of handling an alarm received from a monitoring device alarm, according to certain aspects of the present disclosure. FIG. 8A depicts an exemplary embodiment in how the Alarm Management System 120 depicted in FIG. 1 may classify each category of patient monitor alarms, each with their own separate logic and rules using dynamic attributes to define initial sub-priorities for the alarms within the category. As some monitors have hundreds of different alarms, this flowchart includes only a few exemplary workflows to show how a sub-priority may be defined for each alarm based in part on dynamic attributes associated with the patient, including equipment being used to treat or monitor the patient.

The process 800 starts in FIG. 8A with receipt of an alarm. Step 810 branches depending on whether the alarm is associated with a clinical alarm or a technical alarm. If the alarm is technical, then step 814 determines if the patient monitoring is available or unavailable. For example, monitoring is unavailable when the monitoring loses power, a lead becomes disconnected, the monitor experiences a system error and requires to be taken out of service, etc. This category of alarms covers both the case where all monitoring is lost, e.g. a patient monitor 134 loses power, or when only one of the parameter is not available, e.g. a lead has become disconnected.

Figure 8B:
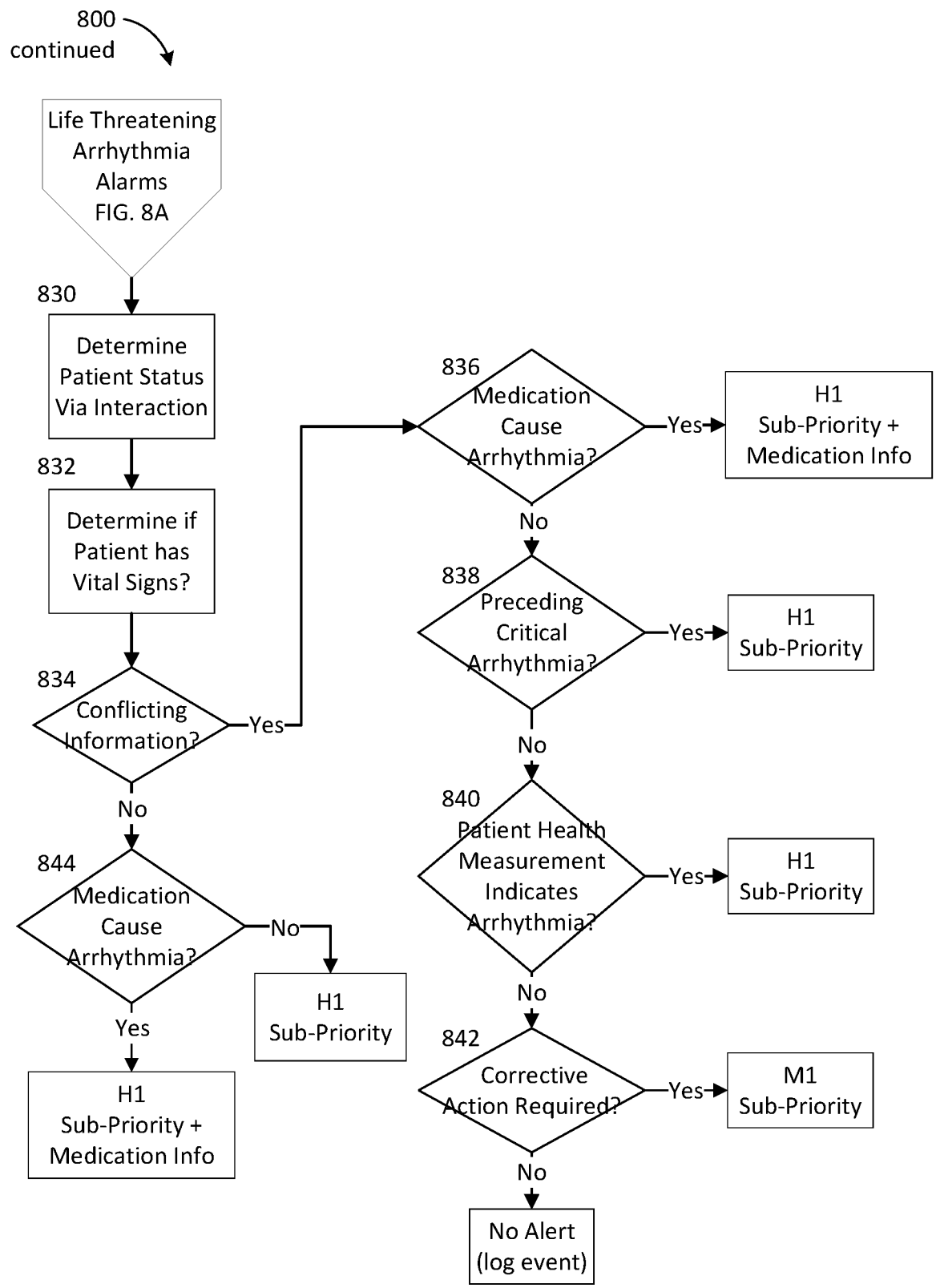
Figure 8C:
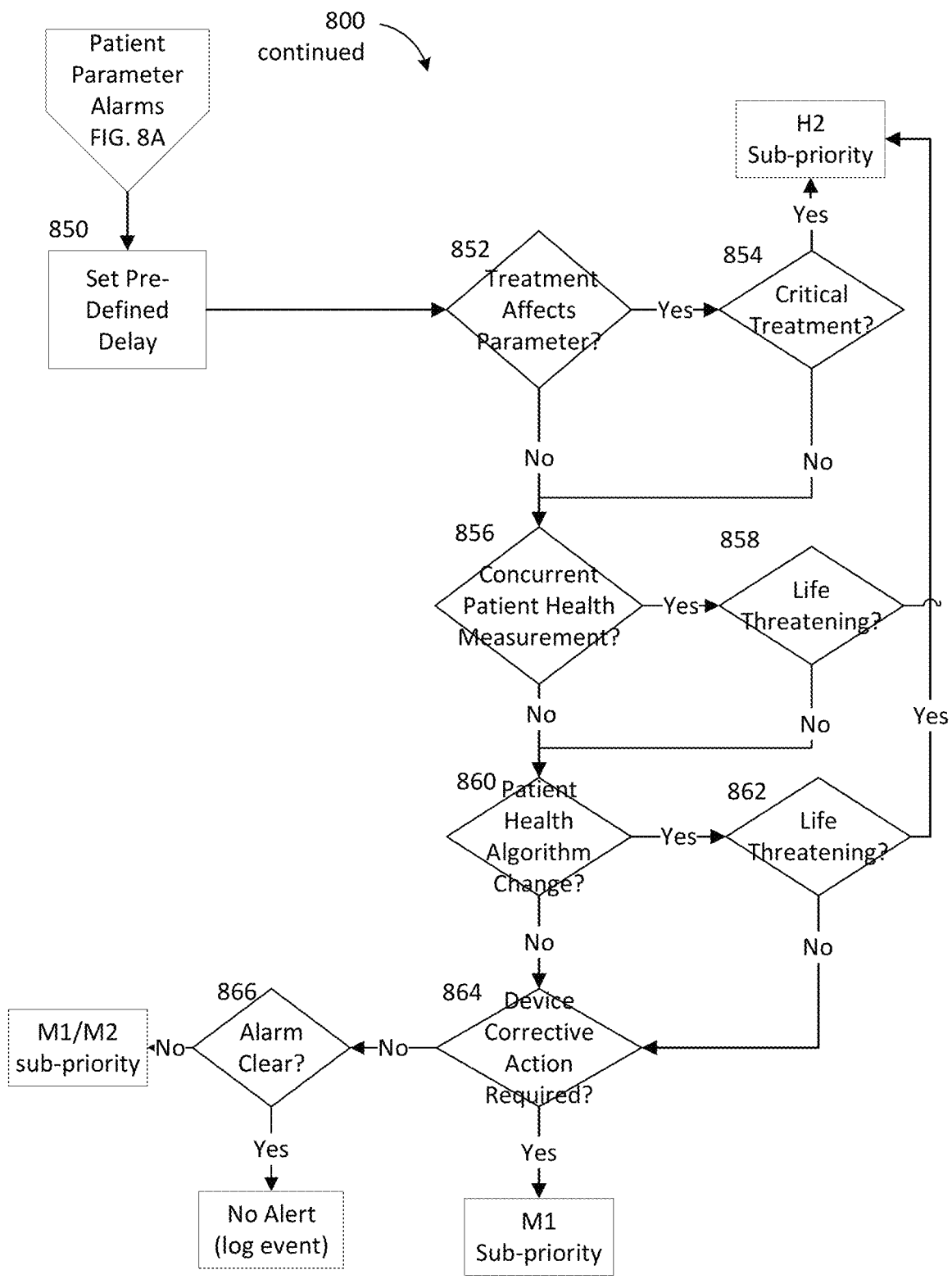
Figure 8D:
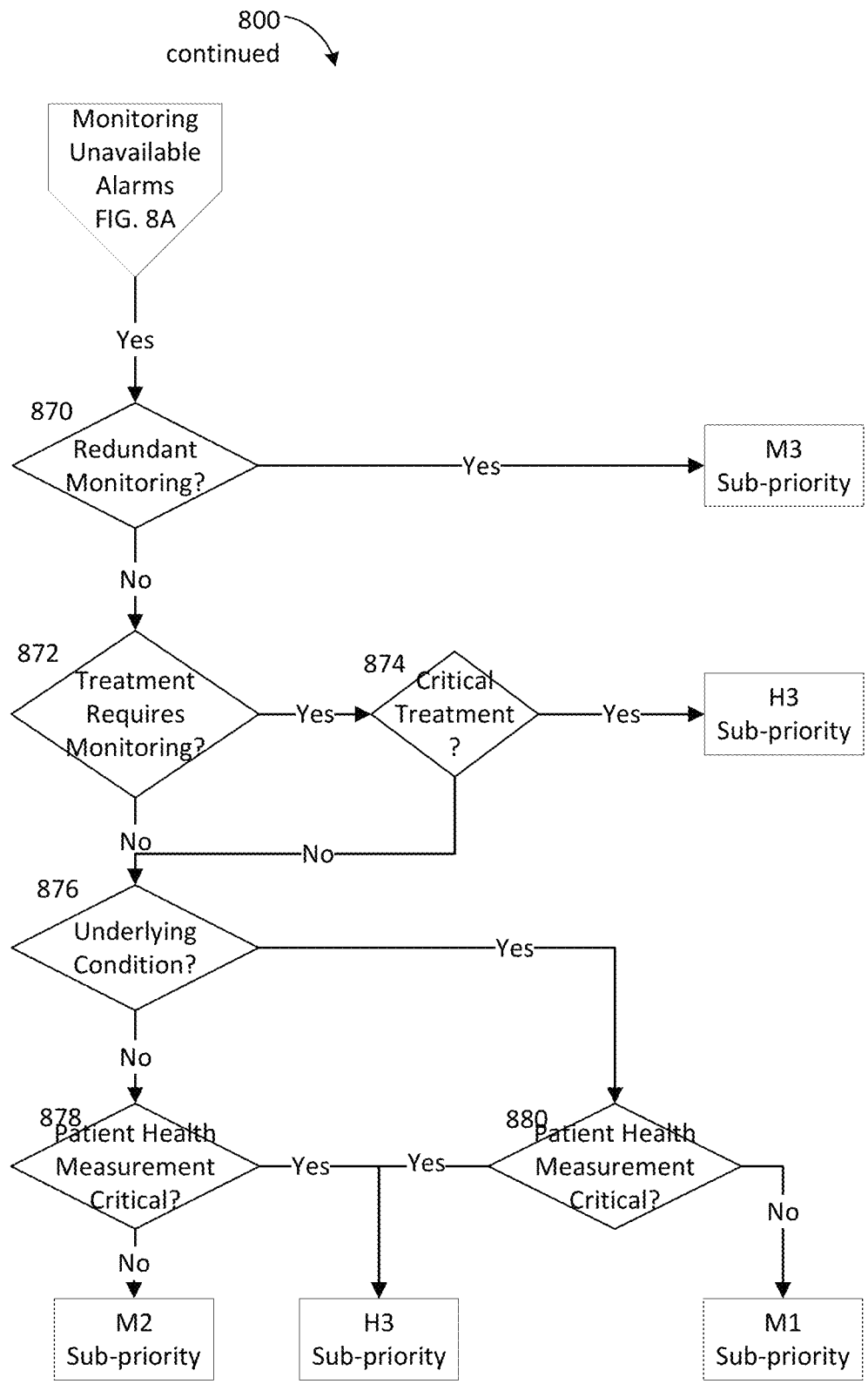

If monitoring is unavailable, then the logic branches to FIG. 8D. If monitoring is available but is unreliable, e.g. due to motion artifact or a potential cause that may weaken a signal, then logic can be developed (not included in this disclosure) similar to, although not necessarily identical to, the logic for handling an absence of monitoring.

If a technical alarm is received while monitoring is available and reliable, then steps 814, 820 direct the process to step 822 that determines whether the alarm requires corrective action. If an action may be required, the process branches to step 824 that determines whether this alarm has an associated time, e.g. the alarm is indicating that a recommended service period has expired and assigns a lower priority if this is a routine timed event. If no corrective action is required, then no alert is generated. If the alarm is clinical in nature, then Steps 812, 816, 818 determine if the alarm is a life-threatening arrhythmia e.g. asystole, ventricular fibrillation, a critical arrhythmia e.g. ventricular tachycardia, a non-critical arrhythmia e.g. premature ventricular contraction, or a patient parameter alarm e.g. heart rate, blood pressure, $SpO_2$, etc. Each of these categories would have their own logic utilizing dynamic attributes to define initial sub-priorities or when to suppress an alarm signal and not send it in an alarm forwarding scheme. Exemplary logic for a life-threatening arrhythmia alarm is described in FIG. 8B and for a patient parameter alarm in FIG. 8C.

FIG. 8B depicts an exemplary process for handling a life-threatening arrhythmia alarm from a patient monitor. Although a true asystole or ventricular fibrillation alarm is always a high priority, the disclosed system can determine if an alarm may be a false positive and therefore not require a high priority sub-priority.

Steps 830, 832 gather information to help determine if the asystole or ventricular fibrillation alarm is a true event. In certain embodiments, step 834 determines if the patient's status is consistent with a life-threatening arrhythmia by determining if an interactive cue from a speaker receives a response in return. In other embodiments, a remote clinician may try to confirm the alarm condition does not exist via Alarm Unit 100, e.g. with the video surveillance camera 118 of FIG. 1, located in the patient's room. In certain embodiments, the system will review the dynamic attributes to determine if there is reliable source of vital sign information that contradicts the asystole or ventricular fibrillation alarm. For example, numerous peer-reviewed articles have confirmed that the presence of certain vital signs, e.g. arterial blood pressure, conflicts with an indication of a life-threatening arrhythmia. If the obtained information does not conflict with the received alarm, then step 834 branches to step 844 that checks whether the patient is on a medication that may cause the arrhythmia and, if confirmatory, assigns an H1 priority and includes this drug information in the alert. Otherwise, an H1 sub-priority is assigned.

If there is conflicting information in step 834 as to whether the patient is truly experiencing a life-threatening arrhythmia, the process branches to step 836 that checks whether the patient is on a medication that may cause the arrhythmia and, if confirmatory, assigns an H1 priority and includes this drug information in the alert.

If the patient is not receiving a medication that could cause an arrhythmia, the process branches to step 838 that determines if the patient has had a preceding critical arrhythmia alarm. A patient with a ventricular bradycardia may experience increasingly serious arrhythmias over time. If a critical arrhythmia alarm has preceded the current alarm, then step 838 assigned an H1 sub-priority. If the patient has no history of these alarms, the process branches to step 840.

Step 840 determines whether one of the patient's health measurements indicates that the patient could develop a life-threatening arrythmia. For example, a patient may have symptoms, or a blood test associated with carbon monoxide poisoning which could lead to a life-threatening cardiac arrhythmia, e.g. ventricular fibrillation. If there is a significant health status information, step 840 assigned an H1 sub-priority.

If there is no underlying conditions, history, or dynamic attribute that suggests the patient is prone to a life-threatening arrhythmia, the process branches to step 842 that assigns a lower priority, e.g. an M1, if the alarm requires a corrective action, otherwise the alarm is logged but not assigned a sub-priority and no alert is issued. A corrective action may be required in this situation if a dynamic attribute has determined the time has expired on the recommended frequency to change the leads, recommending the leads. In certain embodiments, the Alarm Management Application 120 will log the number of nonactionable or false alarms before this current alarm. A high number of false alarms will send a low priority alert, e.g. M1 or M2, to prompt a technician to determine if electromagnetic interference may be causing the false positive alarms or if the monitor should be replaced.

FIG. 8C depicts exemplary process for handling a patient parameter clinical alarm associated with a patient monitor. These alarms may include heart rate, blood pressure, respiratory rate, $SpO_2$, etc. The urgency of responding to parameter alarms depends on the dynamic attributes associated with the patient. In some cases, a higher sub-priority, e.g. H2 or H3, is recommended when a patient parameter is associated with a potential life-threatening situation. In other cases, either a lower sub-priority, e.g. M1 or M2, for an actionable alarm or no alert may be appropriate.

Step 850 applies a pre-defined delay since a patient parameter alarm, e.g. $SpO_2$, is often transitory in nature and the alarm condition resolves within the delay period. Step 854 determines if the patient is on a treatment that may affect the patient parameter alarm. A patient treatment may be the administration of a fluid or medication from an infusion pump to treat low blood pressure, an implantable device, e.g. a pacemaker, to treat an out-of-range heart rate, etc. In certain embodiments, the Alarm Management Application 120 will consider if the fluid or medication is indicated to treat the parameter or may have side effects that affect the parameter. If the patient is on such a treatment, the process branches to step 854 that assigns a high sub-priority, e.g. H2, if the treatment is critical and otherwise branches to step 856.

Step 856 checks whether any patient health measurement can affect this alarm and, if so, the process branches to step 858 that assesses whether the combination of alarm and dynamic attribute is life-threatening. For example, if the initial alarm is associated with a high heart rate but the patient health measurement showed that there was a period of bradycardia before this alarm, then a potentially serious condition Tachy-Brady Syndrome may manifest, which may require the need for an internal pacemaker if symptoms are significant enough. Another example is if the patient alarm is for high blood pressure and one of the patient health measurements, e.g. lab value, associated with the patient is high blood sugar indicating diabetic ketoacidosis then a higher sub-priority is warranted since disease progression is indicated. If there is an indication that the situation is life-threatening, step 858 assigns an H2 sub-priority otherwise routes the process to step 860.

Step 860 determines if the current patient health measurements change the score of a patient health algorithm. Patient health algorithms like the MEWS are used in lower acuity settings, e.g. a medical ward. In certain embodiments, if the score is high enough, then then the process branches to step 862 and if the new algorithm value indicates a life-threatening risk, step 862 assigns an H2 sub-priority that will cause a rapid response team to assess whether the patient should be moved to a higher acuity setting, e.g. ICU. If the patient health algorithm has changed but does not rise to a life-threatening situation, then the process branches to step 864. If the algorithm score has not changed, the process also proceeds from step 860 to step 864.

Step 864 determines whether a corrective action is required on the device to address the alarm. For example, an alarm indicates that the recommend time to change the leads has expired, thus necessitating a clinician or technician changing the leads. In an example, a device parameter has exceeded a limit and based off the dynamic attributes in steps 854, 856 and 860 not being affirmative, the hospital staff has pre-approved an increase or decrease in the limits so the alarm condition does not re-occur. If a corrective action is required, then a M1 sub-priority alarm is generated. If not, the process branches to step 866 to determine whether the alarm has cleared within the initial delay, e.g. self-cleared. If the alarm clears, then no alert is sent to a remote clinician. If the alarm is not resolved, then in certain embodiments a lower priority alarm is assigned, e.g. M1 or M2. In another embodiment, if steps 854, 858, or 862 is not affirmative, e.g. a patient treatment affects the parameter but the treatment is not critical, an M1 sub-priority is assigned. In certain embodiments, the default setting is an M2 sub-priority FIG. 8D depicts the handling of a technical alarm when some aspect of monitoring is not available, e.g. leads are disconnected, a sensor has failed, etc. In conventional systems, a loss of patient monitoring is uniformly assigned a medium priority alarm. As with patient parameters, the system disclosed herein assesses related dynamic attributes and adjusts the sub-priority up or down based on this additional information, thereby alleviating alarm fatigue.

Step 870 determines if there is redundant monitoring in place. In certain embodiments, if the $SpO_2$ probe is disconnected, which is one of the more frequent monitoring alarms in a hospital, but end tidal $CO_2$ is being measured via capnography, then a low sub-priority, e.g. an M3, is assigned.

If there is not a viable redundant monitoring process in place, the process branches to step 872 that determines whether the patient is undergoing a treatment that requires monitoring associated with the alarm. For example, treating high blood pressure with a medication requires blood pressure monitoring and loss of the blood pressure monitoring assigns an H3 sub-priority. For the same example of a patient being treated for high blood pressure, loss of the $SpO_2$ monitoring would be considered a "no" and the process would branch to step 876.

Step 876 determines if the patient has an underlying condition pertinent to the monitoring being performed. If yes, then the process branches to step 880 that determines if the patient health measurement or other indicator is critical. For example, if the patient is experiencing serious symptoms, has a high patient health algorithm score, or has a critical patient health measurement such as a positive lab test for a cardiac marker, then step 880 assigns a H3 sub-priority. If the patient does not have a critical indicator, a lower sub-priority, e.g. an M1, is assigned.

If the patient does not have an underlying medical condition, the process branches from step 876 to step 878 that will assign an H3 sub-priority if the patient health measurement is critical but assign an even lower sub-priority, e.g. an M2, if their status is not critical.

Aspects

Aspect 1. A method for managing an alarm issued by a medical device being used to treat a patient, comprising the steps: receiving a first alarm from the medical device; retrieving a dynamic attribute associated with the patient; assigning a first sub priority to the first alarm based in part on evaluation of the dynamic attribute; and providing a first alert to a first staff member that is associated with the first sub priority.

Aspect 2. The method of aspect 1, wherein the dynamic attribute comprises a patient monitor factor selected from the group consisting of: a patient health measurement; a change in a patient health algorithm score; and an action by the patient.

Aspect 3. The method of aspect 1, wherein the dynamic attribute comprises a treatment and diagnostic factor selected from the group consisting of: a doctor's order; a patient instruction; and a patient medical record.

Aspect 4. The method of aspect 1, wherein the dynamic attribute comprises a medication factor selected from the group consisting of: an indication for use of a medication or fluid being administered to the patient; and a characteristic of the medication or fluid.

Aspect 5. The method of aspect 4, wherein the medication factor is retrieved from a medication library.

Aspect 6. The method of aspect 4, wherein the medication factor comprises a pharmacokinetic or pharmacodynamic (PK/PD) characteristic of the medication or fluid.

Aspect 7. The method of aspect 1, wherein the dynamic attribute comprises a medical device factor selected from the group consisting of: a setting of the medical device; an operating mode of the medical device; an operational status of the medical device; a measured aspect of the medical device; a secondary mechanism operational in the medical device; an estimated time to perform a corrective action; and a recommended replacement interval of a consumable.

Aspect 8. The method of aspect 1, further comprising the steps of: determining whether the alarm may be caused by an action of the patient; determining whether the patient is able to respond to clinical guidance; and providing clinical guidance to the patient, if it is determined that the patient is able to respond to clinical guidance and that the alarm may be caused by an action of the patient, wherein the clinical guidance comprises a suggestion of an action that the patient should make that may resolve the alarm; and wherein the step of providing the first alert is performed only after a defined time has passed since receiving the alarm without resolution of the alarm.

Aspect 9. The method of aspect 1, further comprising the step of receiving a second alarm, wherein the step of assigning the first sub priority is further based in part on the second alarm.

Aspect 10. The method of aspect 1, further comprising the step of selecting the first staff member from a plurality of staff members that are respectively associated with a plurality of staff roles that are respectively associated with a plurality of sub priorities that includes the first sub priority.

Aspect 11. The method of aspect 10, where the step of selecting the first staff member further comprises selecting a most-junior staff role capable of resolving the alarm.

Aspect 12. A system for managing an alarm issued by a medical device being used to treat a patient, comprising: a processor coupled to at least one of the medical device, a monitoring system being used to monitor the patient, and a hospital system; and a memory coupled to the processor, the memory containing data and instructions that, when loaded into the processor and executed, cause the processor to: receive a first alarm from the medical device; retrieve one or more of first information from the medical device, second information from the monitoring system, and third information from the hospital system, wherein the one or more of the first, second, and third information comprise a dynamic attribute associated with the patient; assign a first sub priority to the first alarm based in part on evaluation of the dynamic attribute; and provide a first alert to a first staff member that is associated with the first sub priority.

Aspect 13. The system of aspect 12, wherein the dynamic attribute comprises a patient monitor factor selected from the group consisting of: a patient health measurement; a change in a patient health algorithm score; and an action by the patient.

Aspect 14. The system of aspect 12, wherein the dynamic attribute comprises a treatment and diagnostic factor selected from the group consisting of: a doctor's order; a patient instruction; and a patient medical record.

Aspect 15. The system of aspect 12, wherein the dynamic attribute comprises a medication factor selected from the group consisting of: an indication for use of a medication or fluid being administered to the patient; and a characteristic of the medication or fluid.

Aspect 16. The system of aspect 15, wherein the medication factor is retrieved from a medication library.

Aspect 17. The system of aspect 15, wherein the medication factor comprises a pharmacokinetic or pharmacodynamic (PK/PD) characteristic of the medication or fluid.

Aspect 18. The system of aspect 12, wherein the dynamic attribute comprises a medical device factor selected from the group consisting of: a setting of the medical device; an operating mode of the medical device; an operational status of the medical device; a measured aspect of the medical device; a secondary mechanism operational in the medical device; an estimated time to perform a corrective action; and a recommended replacement interval of a consumable.

Aspect 19. The system of aspect 12, wherein: the third information further comprises: a plurality of sub priorities associated with the medical device; a plurality of staff roles respectively associated with each of the plurality of sub priorities; and a plurality of staff members respectively associated with the plurality of staff roles; and the first staff member is selected from the plurality of staff members.

Aspect 20. The system of aspect 12, wherein: the data and instructions further cause the processor to receive a second alarm; and assigning the first sub priority is further based in part on the second alarm.

Aspect 21. A method of communicating with a staff member, comprising the steps: receiving an alarm issued by a medical device being used to treat a patient; retrieving a dynamic attribute associated with the patient; selecting a first sub priority based in part on the dynamic attribute; and providing a first alert to a first staff member, wherein the first alert comprises: a first identifier associated with the patient; a second identifier associated with the medical device; the alarm; a dynamic attribute associated with the patient; a value of the dynamic attribute; and a first sub-priority assigned to the alarm based on the dynamic attribute.

Aspect 22. The method of aspect 21, wherein the dynamic attribute comprises a patient instruction.

Aspect 23. The method of aspect 21, wherein the first alert further comprises a recommended corrective action.

Aspect 24. The method of aspect 21, wherein: the medical device is an infusion pump; and the dynamic attribute comprises at least one of an operational status of the infusion pump, a medication being administered by the infusion pump, and a patient health measurement of the patient.

Aspect 25. The method of aspect 21, wherein: the medical device is a patient monitor; and the dynamic attribute comprises at least one of a patient health measurement of the patient and an underlying condition.

Aspect 26. The method of aspect 21, wherein the first alert further comprises: a time duration remaining until the sub-priority will be escalated and a second alert provided.

Aspect 27. The method of aspect 21, further comprising the step of: providing a second alert to a second staff member, wherein the second alert comprises: the first sub-priority; a second sub-priority based in part on the dynamic attribute; and an elapsed time since the alarm was received.

Aspect 28. The method of aspect 27, wherein the second staff member is the same as the first staff member.

Aspect 29. The method of aspect 27, wherein the first alert further comprises: the second staff member; and a sub-priority of an active alarm previously sent to the second staff member.

Aspect 30. A method of silencing an alarm in a room of a patient, comprising the steps of: receiving an alarm from a medical device; causing the medical device to stop emitting an audible alert; retrieving a dynamic attribute associated with the patient; assigning a sub priority to the alarm based in part on evaluation of the dynamic attribute; providing an alert to a staff member that is associated with the first sub priority; and causing, if the first sub-priority exceeds a threshold, an audible alert to be sounded in the patient room.

Headings and subheadings, if any, are used for convenience only and do not limit the invention.

Reference to an element in the singular is not intended to mean "one and only one" unless specifically so stated, but rather "one or more." Use of the articles "a" and "an" is to be interpreted as equivalent to the phrase "at least one." Unless specifically stated otherwise, the terms "a set" and "some" refer to one or more.

Terms such as "top," "bottom," "upper," "lower," "left," "right," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Although the relationships among various components are described herein and/or are illustrated as being orthogonal or perpendicular, those components can be arranged in other configurations in some embodiments. For example, the angles formed between the referenced components can be greater or less than 90 degrees in some embodiments.

Although various components are illustrated as being flat and/or straight, those components can have other configurations, such as curved or tapered for example, in some embodiments.

Pronouns in the masculine, e.g. "his," include the feminine and neuter gender, e.g. "her" and "its" and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "operation for."

A phrase such as an "aspect" does not imply that such aspect is essential to the subject technology or that such aspect applies to all configurations of the subject technology.

A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such as an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A method for managing an alarm issued by a medical device being used to treat a patient, comprising:
    receiving a first alarm from the medical device;
    retrieving a dynamic attribute associated with the patient;
    assigning a sub-priority to the first alarm based in part on evaluation of the dynamic attribute; and
    providing an alert to a first staff member that is associated with the sub-priority.

2. The method of claim 1, wherein the dynamic attribute comprises a patient monitor factor selected from a group consisting of:
    a patient health measurement;
    a change in a patient health algorithm score; and
    an action by the patient.

3. The method of claim 1, wherein the dynamic attribute comprises an identification, treatment, and diagnostic factor selected from a group consisting of:
    a doctor's order;
    a patient instruction; and
    a patient medical record.

4. The method of claim 1, wherein the dynamic attribute comprises a medication factor selected from a group consisting of:
    an indication for use of a medication or fluid being administered to the patient; and
    a characteristic of the medication or fluid.

5. The method of claim 4, wherein the medication factor is retrieved from a medication library.

6. The method of claim 4, wherein the medication factor comprises a pharmacokinetic or pharmacodynamic (PK/PD) characteristic of the medication or fluid.

7. The method of claim 1, wherein the dynamic attribute comprises a medical device factor selected from a group consisting of:
    a setting of the medical device;
    an operating mode of the medical device;
    an operational status of the medical device;
    a measured aspect of the medical device;
    a secondary mechanism operational in the medical device;
    a feature of the medical device;
    a previous nonactionable alarm received from the medical device;
    an estimated time to perform a corrective action; and
    a recommended replacement interval of a consumable.

8. The method of claim 1, further comprising:
    determining whether the alarm may be caused by an action of the patient;
    determining whether the patient is able to respond to clinical guidance; and
    providing clinical guidance to the patient, if it is determined that the patient is able to respond to clinical guidance and that the alarm may be caused by an action of the patient, wherein the clinical guidance comprises a suggestion of an action that the patient should make that may resolve the alarm;
    wherein the step of providing the alert is performed only after a defined time has passed since receiving the alarm without resolution of the alarm.

9. The method of claim 1, further comprising receiving a second alarm, wherein the step of assigning the sub-priority is further based in part on the second alarm.

10. The method of claim 1, further comprising selecting the first staff member from a plurality of staff members that are respectively associated with a plurality of staff roles that are respectively associated with a plurality of sub-priorities that includes the sub-priority.

11. The method of claim 10, wherein the step of selecting the first staff member further comprises selecting a most-junior staff role capable of resolving the alarm.

* * * * *